US009636238B2

(12) United States Patent  
Sanders et al.

(10) Patent No.: US 9,636,238 B2
(45) Date of Patent: May 2, 2017

(54) SYSTEM TO EVALUATE PROSTHETIC SOCKETS

(71) Applicant: University of Washington Through Its Center for Commercialization, Seattle, WA (US)

(72) Inventors: Joan E. Sanders, Sammamish, WA (US); Michael R. Severance, Seattle, WA (US); Katheryn J. Allyn, Seattle, WA (US)

(73) Assignee: University of Washington, Seattle, WA (US)

( * ) Notice: Subject to any disclaimer, the term of this patent is extended or adjusted under 35 U.S.C. 154(b) by 996 days.

(21) Appl. No.: 13/888,147

(22) Filed: May 6, 2013

(65) Prior Publication Data

US 2014/0149082 A1 May 29, 2014

Related U.S. Application Data

(60) Provisional application No. 61/642,977, filed on May 4, 2012.

(51) Int. Cl.
*G06F 17/50* (2006.01)
*A61F 2/50* (2006.01)
(Continued)

(52) U.S. Cl.
CPC .............. *A61F 2/5046* (2013.01); *A61F 2/76* (2013.01); *A61F 2/80* (2013.01); *A61F 2002/505* (2013.01)

(58) Field of Classification Search
CPC ................ A61F 2/80; A61F 2002/5024; A61F 2002/5026; A61F 2002/5027;
(Continued)

(56) References Cited

U.S. PATENT DOCUMENTS 5,691,909 A * 11/1997 Frey .................... G05B 19/4069
700/159
7,840,393 B1 * 11/2010 Whirley ................. G09B 23/28
703/11
(Continued)

OTHER PUBLICATIONS

Wieshce_2004.pdf Wiesche, Industrial Thermoforming Simulation of Automotive Fuel Tanks, Applied Thermal Engineering 24 (2004) 2391-2409.*

(Continued)

*Primary Examiner* — Kamini S Shah
*Assistant Examiner* — Brian S Cook
(74) *Attorney, Agent, or Firm* — Kilpatrick Townsend and Stockton LLP

(57) ABSTRACT

Systems, methods, and software are provided for assessing manufacturing errors of a prosthetic socket to facilitate a clinical assessment of the socket. The embodiments disclosed herein may align and compare a manufactured socket shape to a desired socket shape to determine whether clinically significant errors are present in the manufactured socket. A mean radial error (MRE) may be calculated and compared to a set threshold. If the MRE falls below the threshold an interquartile range (IQR) may be calculated and compared to an IQR threshold. If the IQR falls below the IQR threshold, surface normal angle errors (SNAE) may be calculated and plotted to the surface model. If the SNAE plot does not include closed contour regions, the socket may proceed to patient fitting. If the MRE or IQR thresholds are exceeded, or if the SNAE plot indicates closed contour regions, the socket may be reshaped accordingly, prior to fitting.

19 Claims, 14 Drawing Sheets

(51) Int. Cl.
*A61F 2/76* (2006.01)
*A61F 2/80* (2006.01)

(58) Field of Classification Search
CPC ...... A61F 2002/5036; A61F 2002/5052; A61F 2002/704; A61F 2002/7615; A61F 2/72; A61F 2/7843; A61F 2002/5047; A61F 2002/505; A61F 2002/50; A61F 2/5046; A61F 2/76
USPC .............................................. 703/2, 6, 7, 1
See application file for complete search history.

(56) References Cited

U.S. PATENT DOCUMENTS

| | | | |
|---|---|---|---|
| 8,423,167 B2 | 4/2013 | Sanders et al. | |
| 2006/0251301 A1* | 11/2006 | McNamara, Jr. .... | A61B 6/0435 382/128 |
| 2010/0023149 A1* | 1/2010 | Sanders ................ | A61F 2/5046 700/98 |

OTHER PUBLICATIONS

Sanders_2007.pdf Sanders, J.E., CAD/CAM transtibial prosthetic sockets from central fabrication facilities: How accurate are they? JRRD, vol. 44, No. 3, 2007, pp. 395-406.*
Gilbson_2006.pdf Gibson, I., Advanced Manufacturing Technology for Medical Applications: Reverse Engineering, Software Conversion and Rapid Prototyping.*
Sanders_2005.pdf Sanders, J. , Bader, D.L. , Bouten, C.V.C. , Colin, D. , Oomens, C.W.J. (2005). 'Stump-socket interface conditions'. Pressure Ulcer Research Current and Future Perspectives. Heidelberg, Germany:Springer , 129-147.*
Hoda_1998.pdf Hoda, A., Geometric Design Tolerancing: Theories, Standards and Applications, Springer, 1998.*
M&Ms_2011.pdf Rajomohan, G., Practical Measurement Strategies for Verification of Freeform Surfaces using Coordinate Measuring Machines, Metrol. Meas. Syst., vol. XVIII (2011), No. 2, pp. 209-222.*
Pommert_2003.pdf Pommert, A., Hohne, K.H., Validation of medical volume visualization: A literature review, 13, Mar. 2003.*
Sanders_2005 (Sanders, J. 'Stump-socket interface conditions'. Pressure Ulcer Research Current and Future Perspectives. Heidelberg, Germany:Springer , 129-147, 2005 ).*
Osipa_2010 (Stop Staring: Facial Modeling and Animation Done Right, Wiley Publishing, Inc. 2010).*
Hahmann_2008 (Stefanie Hahmann, Alexander Belyaev, Laurent Bus_e, Gershon Elber, Bernard Mourrain, et al.. Shape Interrogation. Leila De Floriani, Michela Spagnuolo. Shape Analysis and Structuring, Springer, pp. 1-51, 2008, Mathematics and Visualization, 978-3-540-33265-7. <10.1007/978-3-540-33265-7 1>. <inria-00193551>).*
U.S. Appl. No. 13/957,908, filed Aug. 2, 2013 by Sanders et al. (Unpublished.).
Cagle et al., "Amputee socks: Thickness of multiple socks", Technical Note, Prosthetics and Orthotics International, Jul. 26, 2013, 8 pages.
Goh et al., "Development of an integrated CAD-FEA process for belo-knee prosthetic sockets", Clinical Biomechanics 20, 2005, pp. 623-629.
Houston et al., "Automated fabrication of mobility aids (AFMA): Below-knee CASD/CAM testing and evaluation program results", Journal of Rehabilitation Research and Development, vol. 29, No. 4, 1992, pp. 78-124.
Kohler et al., "Comparison of CAD-CAM and hand made sockets for PTB prostheses", Prosthetics and Orthotics International., 1989, vol. 13, pp. 19-24.
Lee et al., "Using computational simulation to aid in the prediction of socket fit: A preliminary study", Medical Engineering & Physics 29 (2007, pp. 923-929.
Portnoy et al., "Real-Time Patient-Specific Finite Element Analysis of Internal Stresses in the Soft Tissues of a Residual Limb: A New Tool for Prosthetic Fitting", Annals of Biomedical Engineering, vol. 35, No. 1, Jan. 2007 (© 2006), pp. 120-135.
Quesada, Ph. D. et al., "Finite Element Analysis of the Effects of Prosthesis Model Alteration on Socket/STUMP Interface Stresses", Proceedings, Seventh World Congress of ISPO, Chicago, Illinois, Jun. 28 to Jul. 3, 1992, 1 page.
Ruder, "CAD CAM trans-tibial temporary prosthesis: analysis and comparison with an established technique", Prosthetics and Orthotics International, 1992, pp. 189-195.
Sanders et al., "Amputee socks: how does sock ply relate to sock thickness?", SAGE, International Society for Prosthetics and Orthotics, Feb. 13, 2012, 11 pages.
Sanders et al., "CAD/CAM Transtibial Prosthetic Cockets From Central Fabrication Facilities: How accurate are they?", Journal of Rehabilitation Research & Development, vol. 44, No. 3, 2007, pp. 395-406.
Sanders et al., "Central Fabrication: carved positive assessment", SAGE, International Society for Prosthetics and Orthotics, Mar. 1, 2011, 10 pages.
Schnell et al., "Management of Pain in the Amputee", Atlas of Limb Prosthetics: Surgical, Prosthetic, and Rehabilitation Principles. Rosemont, IL, American Academy of Orthopedic Surgeons, 2nd edition, 1992, 18 pages.
Silva et al., "Self-reported prosthetic sock use among persons with trasntibial amputation", Original Research Report, Prosthetics and Orthotics International, May 24, 2013, 11 pages.
Silver-Thorn et al., "Sensitivity of Below-Knee Residual Limb/ Prosthetic Socket Interface Pressures to Variations in Socket Design", Northwestern University Prosthetic Research Laboratory and Rehabilitation Engineering Program, Proceedings, Seventh World Congress of ISPO, Chicago, Illinois, Jun. 28 to Jul. 3, 1992, 1 page.
Steege et al., "Design of Prosthetic Sockets Using Finite Element Analysis", Northwestern University Prosthetic Research Laboratory and Rehabilitation Engineering Program, Proceedings, Seventh World Congress of ISPO, Chicago, Illinois, Jun. 28 to Jul. 3, 1992, 1 page.
Topper et al., "An evaluation of computer aided design of below-knee prosthetic sockets", Prosthetics and Orthotics International, 1990, pp. 136-142.
Turkowski, "Transformations of Surface Normal Vectors with applications to three dimensional computer graphics", Apple Technical Report No. 22, Jul. 6, 1990, 9 pages.

* cited by examiner

| Subject | Fabrication Facility | Necessary Clinical Changes |
|---|---|---|
| 1 | d | None |
| 1 | e | Sizing Reduction & Possible Shaping |
| 1 | f | None |
| 2 | d | Sizing Reduction & Possible Shaping |
| 2 | e | Sizing Reduction & Possible Shaping |
| 2 | f | Shaping |
| 3 | a | Sizing Reduction & Possible Shaping |
| 3 | b | Sizing Reduction & Possible Shaping |
| 3 | c | None |
| 4 | a | Sizing Reduction & Possible Shaping |
| 4 | b | Shaping |
| 4 | c | None |
| 5 | d | Sizing Reduction & Possible Shaping |
| 5 | e | Sizing Reduction & Possible Shaping |
| 5 | f | None |
| 6 | a | Shaping |
| 6 | b | Sizing Reduction & Possible Shaping |
| 6 | c | None |
| 7 | a | Sizing Enlargement & Possible Shaping |
| 7 | b | Sizing Reduction & Possible Shaping |
| 7 | c | None |
| 7 | d | Shaping |
| 7 | e | Sizing Reduction & Possible Shaping |
| 7 | f | None |
| 8 | d | Shaping |
| 8 | e | Shaping |
| 8 | f | Shaping |
| 9 | d | Sizing Reduction & Possible Shaping |
| 9 | e | Sizing Reduction & Possible Shaping |
| 9 | f | None |
| 10 | a | Sizing Reduction & Possible Shaping |
| 10 | b | Sizing Reduction & Possible Shaping |
| 10 | c | None |

Figure 4A

| Fab | None | Sizing & Possibly Shaping | Shaping |
|---|---|---|---|
| a | 0 | 4 | 1 |
| b | 0 | 4 | 1 |
| c | 5 | 0 | 0 |
| d | 1 | 3 | 2 |
| e | 0 | 5 | 1 |
| f | 4 | 0 | 2 |

Figure 4B

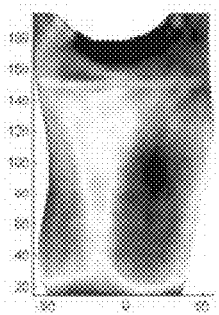
Figure 6A             Figure 6B             Figure 6C
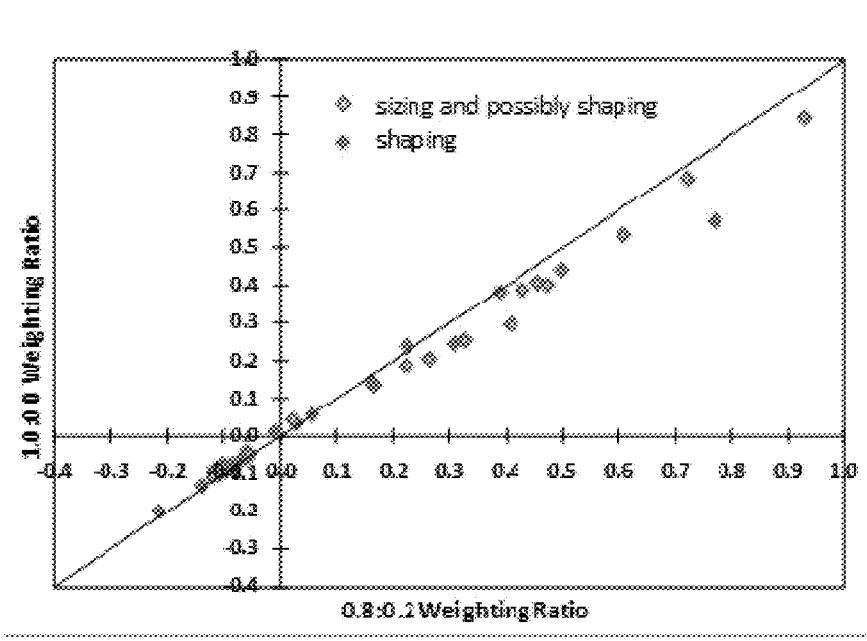
Figure 7

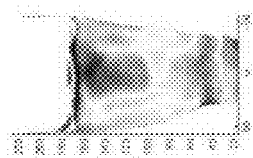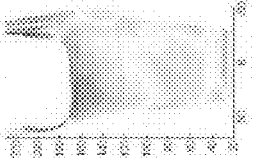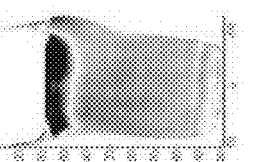

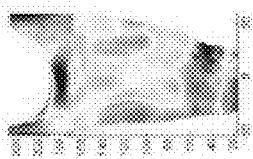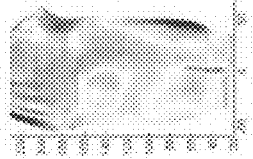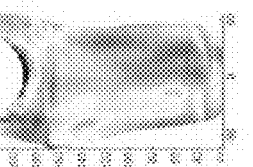

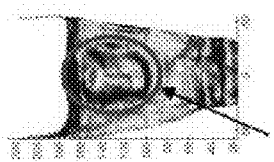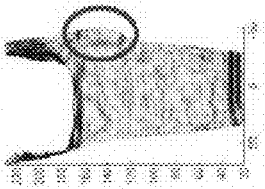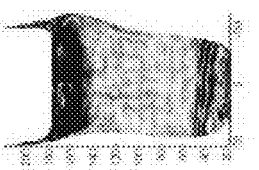

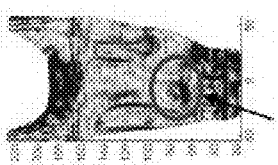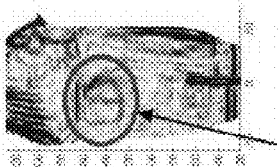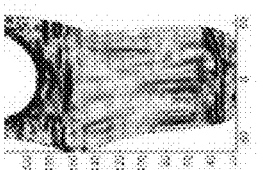
Figure 11A  Figure 11B  Figure 11C

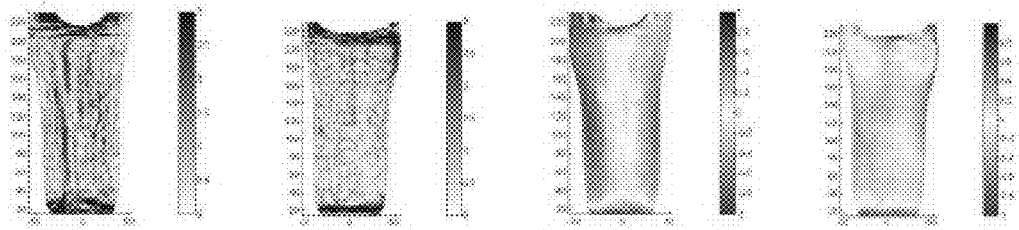
Figure 12A
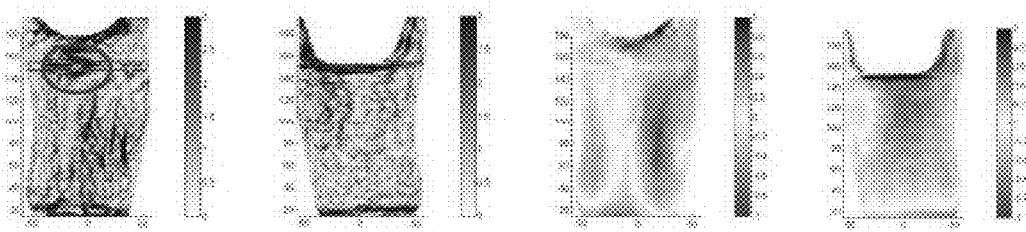
Figure 12B
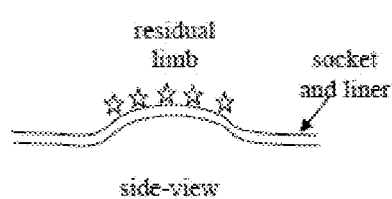
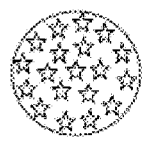
Figure 13A
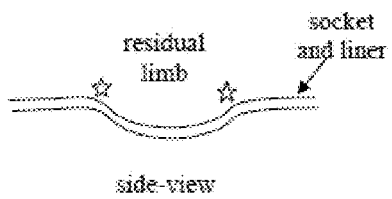
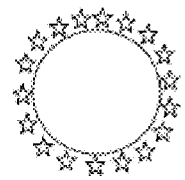
Figure 13B Rates of fluid volume change.

| Variable | Range (%/h) | Median (%/h) | Mean ± SD (%/h) |
|---|---|---|---|
| AM%/h | −8.5 to 5.9 | −3.1 | −2.4 ± 4.0 |
| PM%/h | −5.5 to 1.6 | −1.4 | −1.8 ± 2.4 |
| Between%/h | −2.7 to 0.9 | −1.0 | −1.0 ± 1.0 |
| AM = morning, PM = afternoon, SD = standard deviation. | | | |

SYSTEM TO EVALUATE PROSTHETIC SOCKETS

CROSS-REFERENCES TO RELATED APPLICATIONS

The present application claims benefit to U.S. Provisional Patent Application No. 61/642,977 filed on May 4, 2012, the complete disclosure of which is incorporated herein by reference.

FEDERAL FUNDING STATEMENT

The invention was made with government support under R01 EB004329 awarded by National Institutes of Health (NIH). The government has certain rights in the invention.

BACKGROUND OF THE DISCLOSURE

There are approximately 84,500 to 114,000 new lower-limb amputations each year in the United States. Amputation rates are rising each year, in part because of the rapid increase in diabetes and also because of improvements in treating traumatic injury and vascular disease. More of the patients experiencing these problems are able to live longer but may require limb amputation in order to survive. Further, the recent wars in Iraq and Afghanistan have caused an increase in the number of servicemen and women who undergo an amputation, typically young individuals who are otherwise healthy. Because of the early age at which the amputation occurred, these individuals will be prosthesis users for many years. Thus, there is a strong need to create quality prosthetic limbs for the increasing lower-limb amputee population.

The design of an effective prosthetic socket is crucial to the rehabilitation and overall health of a person with an amputated limb. This point cannot be overemphasized. Most of the time and energy a practitioner applies in making a prosthesis is spent on fabricating the socket that must be fitted to the residual limb. The prosthetic socket must be shaped so that it supports the residual limb in load tolerant areas, while avoiding irritation of sensitive regions on the limb that contact the inner surface of the socket. If these criteria are not achieved, residual limb soft tissue breakdown often occurs when the patient uses the prosthesis. The result of a poor socket fit may include painful sores, blisters, ulcers, or cysts on the residual limb that typically restrict continued prosthesis use, and in severe cases, necessitate a further amputation to a higher anatomical level which can lead to further disability. The incidence of skin breakdown in lower-limb amputees has been reported to be from 24% to 41%. Accordingly, at any one time, as many as 41% of prosthesis users may be experiencing breakdown of the tissue on the residual limb. The principle cause of such breakdown is a poorly fitting prosthetic socket.

Practitioners face challenges in making quality sockets for the increasing amputee population. Also, there is a shortage of prosthetists in the industry, and that shortage is expected to increase in the future, as the demand for prosthetic devices increases. A prosthetist's time is precious and must be used as efficiently as possible. It may be beneficial to improve a prosthetist's efficiency, speed, documentation, repeatability, and quality of fitting a socket to a patient's residual limb, and to ensure a proper socket design early in the process of fitting a prosthetic socket to a recipient.

Modern prostheses are often made using computer-aided-design and computer-aided-manufacturing (CAD/CAM) methods, which were introduced to the prosthetics field about 25 years ago to address these needs. When using a CAD/CAM approach to produce a fitted socket, a practitioner measures the shape of the residual limb using either a cast impression or a commercially-available scanning device that implements one of a number of shape acquisition modalities (e.g., use of a laser scanner, contact hand digitizer, video scanner, structured light projection, or digitization of a plaster cast). The resulting shape is then sent to a custom computer numerical control (CNC) mill, referred to in the art as a "carver," to fabricate a positive model which is then used to form the socket. The practitioner may design a socket on a computer using one of several commercially available software packages and methods. A thermoformer can be used to vacuum form a socket by heating a polymer cone and then vacuum forming it onto the positive model. Alternatively, a thermoplastic sheet can be draped or wrapped over the positive model. After the edges are trimmed, a completed socket is provided and is tested with the patient to determine the acceptability of the fit.

Other methods for socket fabrication exist, including a novel motion guided extrusion technique (referred to as SQUIRT SHAPE™, at Northwestern University), and other rapid prototyping techniques. However, regardless of the method used for fabricating a socket, there is often a quality control problem that arises in the fabrication process, and means are needed to enable a prosthetic socket designer to determine if the fabricated socket indeed accurately matches the shape that was designed. Currently, practitioners creating sockets often spend too much time fixing or remaking the sockets that were produced incorrectly by the CAD/CAM process or the forming process, or both. The benefits of CAD/CAM system, which include improved efficiency, speed, documentation, and lower expense, are substantially reduced or even lost because of this problem. Prosthetists who have an in-office CAD/CAM system suite, central fabrication facilities, and manufacturers of CAD/CAM equipment used to produce sockets could thus benefit from technology for evaluating the quality of each socket produced, to avoid the expense and delay incurred to fix or remake a socket as necessary to achieve a proper fit with the patient's residual limb.

In recent studies, considerable variability was found in the quality of prosthetic sockets fabricated by central fabrication facilities using computer-socket manufacturing methods. Because fabrication errors are often hard to see by eye, they might not be identified by the practitioner until the socket is test fit to the patient. These errors extend the fitting process because they confound clinical fitting. The prosthetist must correct errors both from faulty manufacturing and from incorrect socket design, and it can be difficult to distinguish between the two. Further, if computer-socket manufacturing errors are inconsistent from one fabrication run to the next and the errors are substantial, a practitioner will have difficulty effectively optimizing the socket shape file. This problem might explain why in computer socket design and manufacturing literature there is a wide range in the number of sockets (1 to 5) reported necessary to achieve an acceptable fit. Particularly for young prosthetists, computer-socket manufacturing errors can add significant challenge to prosthetic design.

SUMMARY OF THE INVENTION

Research was conducted to determine what magnitude of socket manufacturing error was clinically relevant and what magnitude was clinically undetectable and thus insignificant. The utility of this effort is to help set manufacturing standards in the prosthetics industry. To accomplish this objective, clinical assessments of socket fit by an experienced practitioner were compared to computer-socket manufacturing errors measured with a shape-sensing instrument. Different computed metrics were developed to identify different kinds of error (volume, shaping), and then evaluated to determine how well the computed metrics matched clinical judgment.

Accordingly, in some embodiments of the present invention, improved systems and methods are provided for objectively assessing a manufactured prosthetic socket. Advantageously, the methods and systems may be used to analyze a prosthetic socket prior to a patient fitting. Thus some defects may be detected using the systems and methods disclosed herein and corrected prior to patient fitting, thereby reducing the number of patient visits needed to provide a prosthetic socket with an acceptable fit. For example in some embodiments, a device is provided that can assess a socket shape after it is manufactured and compare it with an electronic data file that was used to create it. Such files may define a desired shape for the socket and may be stored on a computer hard drive and used for carving the socket positive model.

In some embodiments, a method of assessing a prosthetic socket shape for receiving a residual limb of a patient is provided. The method may comprise the step of calculating surface normal angle errors between points on a first digital model and corresponding points on a second digital model. The first digital model may correspond to the prosthetic socket shape and the second digital model may correspond to a desired shape. For example, the first digital model may comprise a scan of the interior surface of the prosthetic socket. Alternatively the first digital model may comprise a scan of the prosthetic user's residual limb. The second digital model may be a desired prosthetic socket shape or a rectified shape, for example. The method may also comprise the step of plotting the calculated surface normal angle errors to a surface model and thereafter, the operator may accept or reject the prosthetic socket shape in response to the plotted surface normal angle errors.

Optionally, an interior surface of the prosthetic socket may be scanned to create the first digital model. The plotted surface normals angle errors may be displayed to the operator. The second digital model may comprise a digital model of an interior of a patient's currently used socket. In some cases, the method includes the step of calculating an average radial difference between points on the first digital model and corresponding points on the second digital model and determining whether the mean radial error is above or below a set threshold. Optionally, the threshold has a value between 0.24 mm and 0.29 mm. Some methods of may include the step of resizing or reshaping the socket when the mean radial error is above the threshold value. The socket shape may be reduced when the threshold is exceeded.

In some embodiments, the method includes the step of determining whether an interquartile range of radial error is above or below a second threshold. The second threshold value may have a value between 0.34 mm and 0.42 mm. The socket may be regionally reshaped when the interquartile range of radial error is above the second threshold value.

The method may include the step of identifying a local bulge or indentation corresponding to a closed contour region in the surface normal angle error plot. A portion of the socket may be locally reshaped at a portion of the socket corresponding to the identified closed contour region.

In another embodiment of the present invention a method of objectively assessing a prosthetic socket shape to facilitate an assessment of the prosthetic socket shape is provided. The method may include the step of aligning a first digital model with a second digital model using an alignment function. The alignment function may depend on a volume difference between the first digital model and the second digital model. Similar to the method above, the first digital model may correspond to the prosthetic socket shape and the second digital model may correspond to a desired shape. The method may also include the step of calculating an average radial difference between points on the first digital model and corresponding points on the second digital model and the step of determining whether the mean radial error is above or below a first threshold, the first threshold having a value greater than 0.18 mm.

The method may further include the step of scanning an interior surface of the prosthetic socket to create the digital model of the interior surface. Optionally, the first threshold may have a value between 0.24 mm and 0.29 mm. The method may further include the step of resizing or reshaping the socket when the mean radial error is above the first threshold. Additionally the method may further include the step of determining whether an inner quartile range of radial error is above a second threshold value when the mean radial error is below the first threshold value. Optionally, the method may include the step of resizing or reshaping the socket when the interquartile range of radial error is above the second threshold. Surface normal angle errors may be calculated between points on the first digital model and corresponding points on the second digital model. The calculated surface normal angle errors may be plotted to a surface model when the interquartile range of radial error is below the second threshold.

In yet another embodiment of the present invention, a method of objectively assessing a prosthetic socket shape to facilitate an assessment of the prosthetic socket shape is provided. The method may include the step of calculating radial differences between points on a first digital model and corresponding points on a second digital model. Again, the first digital model may correspond to the prosthetic socket shape and the second digital model may correspond to a desired shape. The interquartile range of radial error may be determined and compared to a threshold value. The threshold value may have a value greater than 0.3 mm.

The first digital model may be created by scanning the interior surface of the prosthetic socket. Optionally the threshold may have a value between 0.34 mm and 0.42 mm. The prosthetic socket may be reshaped or resized when the interquartile range of radial error is above the second threshold value. In some embodiments surface normal angle errors between the first digital model and the second digital model may be plotted to a surface model when the interquartile range is below the threshold.

In another embodiment of the present invention, a system for assessing a prosthetic socket shape is provided. The system may include an alignment module for aligning a first digital model with a second digital model based at least on a volume difference between the first digital model and the second digital model. The system many also include an analysis module configured to calculate surface normal angle errors between points on the first digital model and corresponding points on the second digital model. The analysis module may be further configured to plot the surface normal angle errors to a surface model.

The system may include an input module configured to receive the first digital model from a scanning system and the second digital model from a reference database. A scanning system may be coupled with the input module. The analysis module may be configured to output the surface model to a display for practitioner viewing. In some embodiments the analysis module is further configured to calculate radial errors between points on the first digital model and corresponding points on the second digital model and to determine whether a mean radial error exceeds a mean radial error threshold. The analysis module may be further configured to calculate radial errors between points on the first digital model and corresponding points on the second digital model and to determine whether an interquartile range of radial error exceeds an interquartile range threshold.

In yet another embodiment of the present invention, a system for assessing a prosthetic socket shape is provided where the system includes an alignment module for aligning a first digital model with a second digital model based at least on the a volume difference between the first digital model and the second digital model and an analysis module configured to calculate an average radial difference between points on the first digital model and corresponding points on the second digital model. The analysis module may be further configured to determine whether the mean radial error is above or below a set threshold. The threshold may have a value greater than 0.18 mm. Optionally the threshold has a value between 0.24 mm and 0.29 mm.

In yet another embodiment of the present invention a system for assessing a prosthetic socket shape is provided where the system includes an alignment module for aligning a first digital model with a second digital model based at least on a volume difference between the digital model and the desired shape and an analysis module configured to calculate radial differences between points on the first digital model and corresponding points on the second digital. The analysis module may be further configured to determine whether an interquartile range of radial error is above or below a set threshold. The threshold may have a value greater than 0.3 mm. Optionally the threshold has a value between 0.34 mm and 0.42 mm.

In another embodiment of the present invention, a non-transitory computer-readable storage medium comprising a set of computer executable instructions for facilitating clinical assessment of a prosthetic socket shape is provided. The execution of the instructions by a computer processor may cause the processor to carry out the steps of aligning a first digital model with a second digital model using an alignment function, the alignment function at least depending on a volume difference between the first digital model and the second digital model. The processor may also analyze the socket shape by performing at least one of the following: (1) calculating an average radial difference between points on the first digital model and corresponding points on the second digital model and providing a first signal when the mean radial error exceeds a first threshold (the first threshold may have a value greater than 0.18 mm); (2) calculating radial differences between points on the first digital model and corresponding points on the second digital model and providing a second signal when an interquartile range of radial error is above a second threshold (the second threshold may have a value greater than 0.3 mm); and (3) calculating surface normal angle errors between points on the first digital model and corresponding points on the second digital model and plotting the calculated surface normal angle errors to a surface model. The processor may output one of the first signal, the second signal, and the surface model to an operator.

Optionally, the processor may further carry out the step of receiving the first digital model from a scanning system. The first threshold value may be between 0.24 mm and 0.29 mm in some embodiments. Additionally the second threshold value may be between 0.34 mm and 0.42 mm in some embodiments.

Although this exemplary embodiment has been described in great detail above, many variations are available. Further features of the invention, its nature and various advantages will be more apparent from the accompanying drawings and the following detailed description.

BRIEF DESCRIPTION OF THE DRAWINGS

FIGS. 4A-4B show the results from clinical test fittings— FIG. 4A shows the results grouped by subject and FIG. 4B shows the results grouped by central fabrication facility;

FIGS. 6A-6C show exemplary radial error results plotted on the corresponding surface model;

FIG. 7 shows mean radial error results using different weighting ratios in the socket alignment optimization algorithm;

FIGS. 11A-11C show exemplary surface normal angle error results for sockets with mean surface normal angle errors greater than 4.0°. The left two panels show surface normal angle error (units are degrees) and the right two panels show radial error (units are mm);

FIGS. 12A-12B show exemplary surface normal angle error results for sockets with mean surface normal angle errors less than or equal to 4.0°. The left two panels show surface normal angle error (units are degrees) and the right two panels show radial error (units are mm);

FIGS. 13A-13B illustrate stress concentrations for concave and convex socket shaping errors;

DETAILED DESCRIPTION OF THE INVENTION

Figure 1:
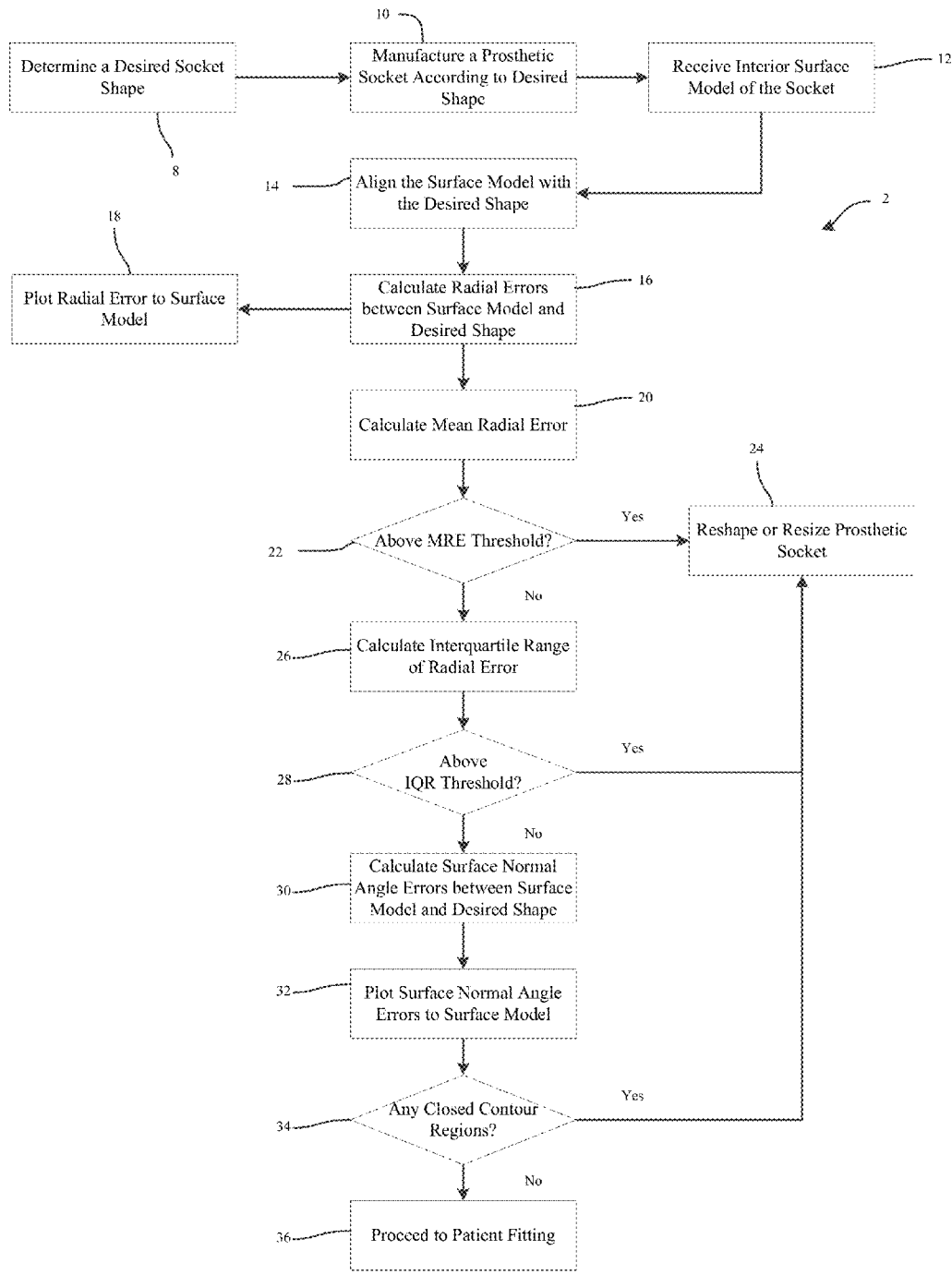
FIG. 1 illustrates an exemplary method according to some embodiments of the present invention.

Computed metrics that have clinical meaning empower the practitioner and the industry with tools. The computed metrics developed here may help define how much computer-socket manufacturing error is allowable before it is clinically relevant to fit. The metrics may serve as tools for quantitative evaluation of manufactured socket quality. Sockets from different central fabrication facilities may be compared and, further, the same facility can test how different design variables affect quality. For example, the influence of different pre-form materials, carving speeds, or bit sizes on manufactured socket shape can all be tested. This insight should be useful to central fabrication facilities and their clients, and also to clinics using in-house CAD/CAM who seek to optimize clinical outcome of their socket manufacturing practices. It would also be interesting to use these tools to compare thermoplastic and laminated sockets. In some embodiments, the insight gained in this research into relationships between socket shape error and clinical assessment of socket fit may be applicable to the socket design stage of making a prosthesis. Computational tools may additionally extend and enhance practitioner CAD socket design efforts.

MRE, IQR, and SNAE may serve as effective metrics to characterize quality of computer-manufactured prosthetic sockets for people with trans-tibial limb loss. Comparison of the metrics with practitioner assessment of socket fit showed that: (1) an MRE greater than about 0.25 mm may be associated with clinical need for socket reduction; (2) an IQR greater than about 0.4 mm may be associated with clinical need for sizing or shape modification; and (3) a closed contour of elevated SNAE may be associated with clinical need for shape modification at the closed contour.

In some embodiments, clinically-appropriate threshold values can be recommended for MRE, IQR, and SNAE, or other criteria defined. Alternatively or additionally, some patients may have more relaxed metric criteria than others (young traumatic injury patient vs. bony elder dysvascular patient, for example). In some embodiments, different polymers, e.g. ones that undergo much shrinkage vs. those that do not, may contribute to sizing error (MRE, IQR) or shaping error (SNAE). Alternatively or additionally, process variables may also contribute to different MRE, IQR, and/or SNAE results. For example, (1) cooling time to transport the socket from the oven to the model and apply vacuum, (2) different technicians within a facility performing the manufacturing process, and/or (3) other process variables may generate different MRE, IQR, and/or SNAE results.

An extension of the present study is investigation of variable geometry sockets. Variable geometry sockets are a technology in prosthetics (e.g., Active Contact System, Simbex) that allows socket shape to be altered so as to accommodate diurnal or long-term volume changes in the residual limb. In some embodiments, variable geometry sockets require the practitioner to set adjustment of maximum and minimum socket volume so that the socket is effective and safe for the patient. The alignment algorithm and computed metrics described in the present study allow investigators to determine if shape adjustments need to be made in specific regions or if a global volume adjustment is acceptable. In addition, they facilitate a determination of what range of socket shapes may be appropriate for a patient.

FIG. 1 illustrates an exemplary method 2 for objectively analyzing a manufactured prosthetic socket according to some embodiments of the present invention. At step 8, a desired socket shape is determined. Thereafter, at step 10, a prosthetic socket may be manufactured per the desired socket shape. At step 12, a model of the interior surface of the socket may created by scanning the interior surface of the socket with a scanning system. At step 14, the surface model may be aligned with the desired socket shape. At step 16, after the surface model and reference are aligned, radial errors may be calculated between points on the surface model and corresponding points on the reference. Optionally, the calculated radial errors may be plotted 18 to the surface model and displayed to a practitioner. At step 20, a mean radial error ("MRE") may be calculated based on the error values calculated at step 16. The mean radial error may be compared to a mean radial error threshold to determine whether the calculated mean radial error exceeds the set threshold. If the MRE exceeds the threshold, a practitioner may reshape or resize the prosthetic socket 24 as necessary, even before fitting the prosthetic socket to the patient. If the MRE does not exceed the threshold value, the practitioner may then calculate the interquartile range ("IQR") of radial error 26. At step 28, the practitioner may then determine whether the calculated IQR exceeds a set IQR threshold. If the IQR threshold is exceeded, the practitioner may reshape or resize the prosthetic socket 24 accordingly. If the IQR is satisfactory, the surface normal angle errors ("SNAE") between points on the surface model and the reference may be calculated 30. The calculated SNAE between the surface model and the reference may be plotted to the surface model 32 and displayed to the practitioner. At step 34, any closed contour regions on the surface model may be identified using the SNAE plot. If the practitioner identifies a closed contour region, the prosthetic socket may be unacceptable and reshaped or resized 24 as necessary. If closed contour regions are not present on the SNAE plot, the practitioner may then proceed to patient fitting 36 to determine whether the socket provides an acceptable fit.

Figure 2:
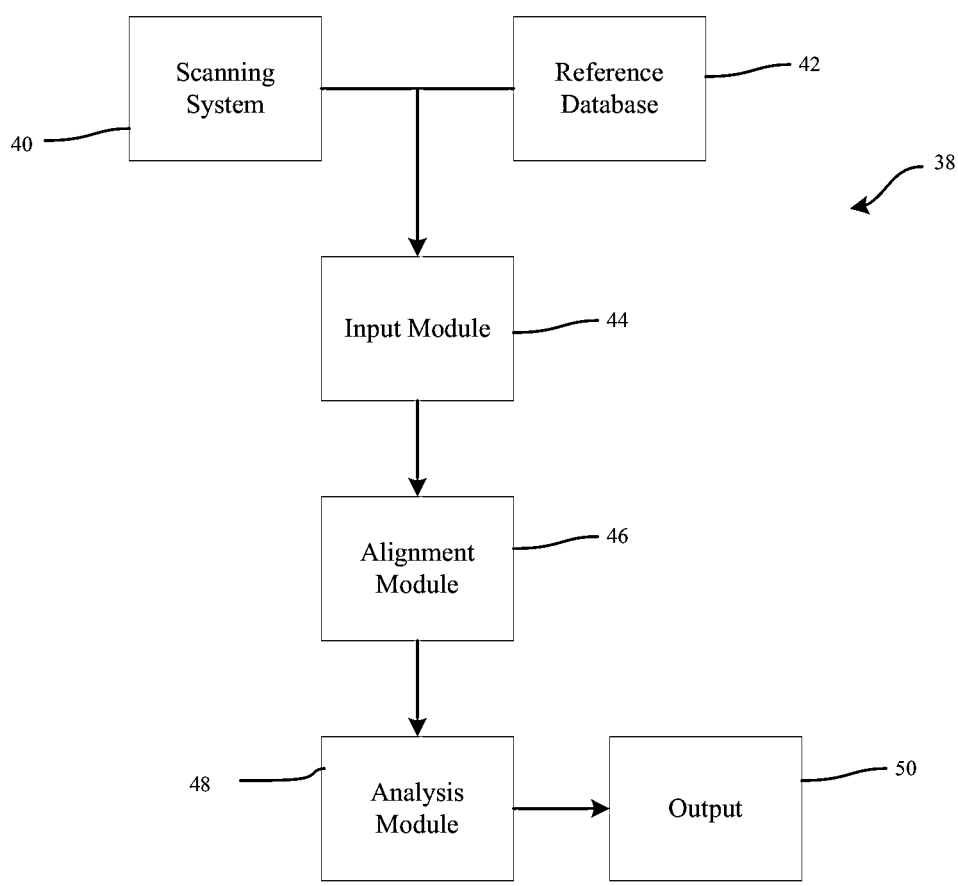
FIG. 2 illustrates an exemplary system according to some embodiments of the present invention.

FIG. 2 illustrates an exemplary system 38 according to some embodiments of the invention which may be used to practice exemplary method 2. An input module 44 may be coupled with a scanning system output 40 and a reference 42. The scanning system output 40 may define the interior surface of a manufactured prosthetic socket. The reference 42 may correspond to a desired prosthetic socket shape. An alignment module 46 may be coupled with the input module 44 and may be configured to align a received model of the prosthetic socket and the reference. An analysis module 48 may be coupled to the alignment module 46 and may be configured to calculate a radial errors, interquartile ranges, and surface normal angle errors between the model and the reference. The results from the analysis module 48 may then be sent to an output 50 so that the practitioner may interpret the results.

The exemplary method 2 in FIG. 1 proceeds similar to clinical static-fitting assessment in that socket volume, then regional volume, and then local shape were evaluated. This strategy may well-identify error and it may also simplify interpretation of computational results by indicating the nature of the error. At step 8, a desired socket shape may be determined for a patient. The desired socket shape may correspond to an electronic shape file for another prosthetic socket, a residual limb that the prosthetic socket is designed to fit, a positive model of the residual limb that the prosthetic socket is designed to fit, a positive model of the intended socket shape, etc. In the research conducted to pursue quality standards for computer-manufacturing of prosthetic sockets for people, thirty-three test sockets were designed 8 as duplicates of the participants' normally used sockets and fabricated 10 using central fabrication facilities. Human subject volunteers were included in this investigation if they had a trans-tibial amputation at least twelve months prior and were a limited community ambulator or more active (Medicare Functional Classification Level (MFCL)≥K2).

Since the test sockets were intended as duplicates of the participants' normally used sockets, an additional inclusion criterion for the study was that the subject regularly used an acceptably fit definitive prosthesis, as deemed in clinical exam by the research practitioner. It was preferable if the prosthetic socket fit properly with less than 10 ply of sock thickness between the residual limb and socket. A socket with sock thickness greater than 10 ply may indicate a poorly fitting socket.

In order to determine the desired shape 8, the shape of the inside of each subject's regular prosthetic socket from the patellar tendon to as far distally as possible was measured using a custom instrument described in related U.S. patent application Ser. No. 12/507,560, entitled Computer Aided Design and Manufacturing of Transtibial Prosthetic Sockets and Sanders J E, Rogers E L, Sorenson E A, Lee G S, Abrahamson D C. *CAD/CAM transtibial prosthetic sockets from central fabrication facilities: How accurate are they*? J Rehabil Res Dev. 2007; 44(3):395-406, the entire disclosures of which are incorporated herein by reference. The instrument was a very accurate mechanical digitizer that measured the position relative to a stable base of a low friction sapphire ball (3.2 mm diameter) mounted to the tip of a spring-loaded stylus arm. The sapphire ball contacted the inside surface of the socket while the socket was rotated about its longitudinal axis using a stepper motor in the base (SM232AE-NGSN, Compumotor). After a cross-section was digitized the stylus arm was moved up using a linear slide rail (ETB32-B08PA99-HRB450L-A, Parker-Daedal), and the next cross-section was digitized.

The angle of the stylus arm relative to the socket longitudinal axis was measured using a rotational variable differential transformer (RVDT) (R30A and ATA 2001, Schaevitz) mounted to the top of the stylus arm, and its vertical position was measured using a linear differential transformer (LDT) (BTL-5-A/C/E/G1-M457-R-S32, Balluff) within the linear slide rail. In post-processing algorithms, vertical translation of the stylus tip from rotation of the stylus arm about the RVDT axis was corrected. The instrument had a radial resolution better than 0.08 mm and measured socket volume differences less than 0.1%. Each socket was measured from the patellar tendon to the distal end at cross-sections spaced at 0.8 mm. A total of 800 points were measured in each cross-section at angular increments of 0.45°. It took approximately 6 h to digitize each socket shape.

To measure the shape of the prosthetic socket above the patellar tendon, a different instrument was used. After blocking with tape the proximal anterior and posterior sections, the socket was positioned in a commercial digitizer (Provel). Use of the tape ensured that the stylus probe had continuous contact surface during digitization. Unlike the prior instrument, the Provel digitizer was able to digitize the upper socket effectively because the contact probe was large (a 2.0 cm diameter disk) and did not get stuck in the crevices between the socket and tape. The digitizer sampled at 120 points per slice at a 5.0 mm slice spacing. After digitizing the entire socket, a custom alignment algorithm was used, which is described below, to align the shape measured with the custom instrument with the shape measured using the Provel digitizer. The sections common to both shapes were aligned. The proximal socket section from the Provel digitizer was added to the scanner data to make a single electronic shape file for the entire socket. There was error in the proximal section measurement because the Provel digitizer, not intended for detailed investigation of socket shape differences but instead for capturing residual limb cast shape was not as accurate as the custom shape measurement instrument. Impact of this error on shape analysis results may be taken into account. Using the data, an AAOP formatted file was created at 90 points per slice at 0.8 mm spacing. The file was used as the desired socket shape 8 and for fabrication of test sockets 10.

While the above scanners were used for the clinical study, the present technology is not limited by the type of scanner used. For example, the present technology may be integrated with or used in connection with advancing imaging technology, once imaging technology is developed to measure the inside shape of a socket with sufficient speed, accuracy, and sensitivity to be implemented in computer fabrication equipment and to be useful to prosthetic socket manufacturing evaluation. Incorporating quantitative metrics into computer socket manufacturing practice, for example, to reduce socket fabrication error, may make computer-socket fabrication more cost effective than traditional techniques. Presenting manufacturing error information to practitioners may extend clinical capabilities, enhance judgment, and reduce time to effectively fit prosthetic sockets to patients. Properly indicating the nature of the error allows the technology to extend the practitioner's capabilities in a manner not previously possible.

For the fabrication of test sockets 10, the socket may be manufactured using conventional methods and systems. For example, the research study described above utilized six central fabrication facilities to make test sockets for the subjects. Each facility made a clear check socket of PETG (glycol-modified polyethylene terephthalate) material and returned it untrimmed at the brim.

The shape of the fabricated test socket may be measured 12 using the custom shape-sensing instrument described above or any other currently available or later developed scanning system. Since the sockets used for the research study were untrimmed, the entire socket could be digitized with the custom instrument alone; it was not necessary to use the Provel digitizer to measure the proximal aspect of the socket. After digitization 12, the research practitioner trimmed the socket and filed the brim using standard clinical procedures. In some embodiments of the invention, a manufactured socket may be trimmed prior to scanning and may be scanned using two or more different scanning devices as needed. In such embodiments, the two or more scans may be aligned according to common features to create the interior surface model of the socket 12.

To assess the shape quality of the computer manufactured sockets, the test socket shapes may be aligned and compared with the desired socket shapes for each subject. To align the shapes 14, an optimization procedure may be implemented that involves a combination of minimizing the volume difference and maximizing the shape similarity. Optionally, the optimization procedure may minimize the volume difference only. An exemplary alignment algorithm and mathematical functions used in the optimization for the research study are described below:

Transforming Surface$_2$ to Surface$_1$

Matrix conventions for transforming surface points and surface normals between two surfaces are described below. The conventions are the standard nomenclature used in the field of geometric morphometrics. See Foley J D, van Dam A, Feiner S K, Hughes J F. *Computer Graphics: Principles and Practice in C, 2$^{nd}$ Edition*. Addison-Wesley, 1996, the full disclosure of which is incorporated herein by reference.

Let $$d_2 = [x\ y\ z\ 1] \quad (1)$$

be a set of points on Surface$_2$ and $$n_2 = [nx\ ny\ nz\ 1] \quad (2)$$

be a set of surface normals on Surface$_2$. The first three terms in each vector represent magnitudes for the three directions (x,y,z). The fourth term is a scaling terms. Because no scaling is performed in this exemplary optimization, the fourth term may be set to a value of 1.

The translations and rotations to transform the data from Surface$_2$ to Surface$_1$ may be defined as:

$$T = \begin{bmatrix} 1 & 0 & 0 & 0 \\ 0 & 1 & 0 & 0 \\ 0 & 0 & 1 & 0 \\ T_x & T_y & T_z & 1 \end{bmatrix} \quad (3)$$

$$R_x = \begin{bmatrix} 1 & 0 & 0 & 0 \\ 0 & \cos\theta_x & \sin\theta_x & 0 \\ 0 & -\sin\theta_x & \cos\theta_x & 0 \\ 0 & 0 & 0 & 1 \end{bmatrix} \quad (4)$$

$$R_y = \begin{bmatrix} \cos\theta_y & 0 & -\sin\theta_y & 0 \\ 0 & 1 & 0 & 0 \\ \sin\theta_y & 0 & \cos\theta_y & 0 \\ 0 & 0 & 0 & 1 \end{bmatrix} \quad (5)$$

$$R_z = \begin{bmatrix} \cos\theta_z & \sin\theta_z & 0 & 0 \\ -\sin\theta_z & \cos\theta_z & 0 & 0 \\ 0 & 0 & 1 & 0 \\ 0 & 0 & 0 & 1 \end{bmatrix} \quad (6)$$

where $T_x$, $T_y$, and $T_z$ are translations along the x, y, and z axes, and $\theta_x$, $\theta_y$, and $\theta_z$ are rotations about the x, y, and z axes. The goal of the alignment algorithm described below is to determine $T_x$, $T_y$, $T_z$, $\theta_x$, $\theta_y$, and $\theta_z$.

During the exemplary optimization process, $T_x$, $T_y$, $T_z$, $\theta_x$, $\theta_y$, and $\theta_z$ are real numbers (after an initial guess of [0 0 0 0 0 0], they are calculated in each iteration). The transformation matrix to transform Surface$_2$ to Surface$_1$ may be defined as:

$$M_{2to1} = T R_x R_y R_z \quad (7)$$

Thus the operation to transform the set of points on Surface$_2$ to Surface$_1$ may be defined as:

$$d_1 = d_2 M_{2to1} \quad (8)$$

To transform the data back to Surface$_2$, the inverse of the transformation matrix may be used:

$$M_{1to2} = M_{2to1}^{-1} \quad (9)$$

$$d_2 = d_1 M_{1to2} \quad (10)$$

Surface normals are not transformed the same as surface points. To transform the surface normal vector, the inverse transpose of the transformation matrix may be used, see Turkowski K., *Transformations of surface normal vectors with application to three dimensional computer graphics*. Technical Report No. 22, Apple Computer, Inc., 1990, the full disclosure of which is incorporated by reference:

$$N_{2to1} = [M_{2to1}^{-1}]^T \quad (11)$$

$$n_1 = n_2 N_{2to1} \quad (12)$$

To transform the surface normal vector back to Surface$_2$ the inverse of the transformation matrix may be used:

$$N_{1to2} = N_{2to1}^{-1} \quad (13)$$

$$n_2 = n_1 N_{1to2} \quad (14)$$

Alignment Algorithm

1. Fit Dataset #1 (the normally-used socket) with a tensor product B-spline to create Surface$_1$. A tensor product B-spline surface is the result of a tensor product of two B-spline curves. The surface may be defined by a rectilinear grid of control points. See Farin G, Hansford D. The Essentials of Computer Aided Graphic Design. A. K. Peters, Ltd. Natick, Mass., 2000, the full disclosure of which is incorporated herein by reference.

2. Fit Dataset #2 (the test socket) with a tensor product B-spline to create Surface$_2$.

3. Sample Surface$_1$ at an evenly-spaced [θ,z] grid, defining the new set of points as:

$$d_1^A = [x\ y\ z\ 1] \quad (15)$$

Calculate the surface normals at each of these points and define them as:

$$n_1^A = [n_x\ n_y\ n_z\ 1] \quad (16)$$

Note that in the optimization process described below, the normal vectors may be unit vectors.

4. Input optimization parameters. Provide initial guess of $T_x$, $T_y$, $T_z$, $\theta_x$, $\theta_y$, and $\theta_z$. Use [0 0 0 0 0 0]. Note that to use this initial guess, it is preferable if the two datasets are reasonably well aligned at the outset. In the research study this was accomplished by taking care when setting up the sockets in the digitizer so that the z-axis was well aligned with the centroids of the socket cross-sections, and the stylus arm at the outset of digitizing was at a tangential position corresponding to the center of the patellar tendon bar.

4a. Set limits on translation and rotation. In the present study translation limits of −40 mm to +40 mm and rotation limits of −45° to 45° were used.

4b. Specify use of the active set algorithm. "Active set" is a Matlab term indicating that the gradient of the objective function is not to be provided by the user.

4c. Set termination tolerance on the solution. In the present study a value of 10$^{-6}$ was used.

5. Run the optimization routine with a Radial Weight of 1.0 and a NormalWeight of 0.0 to completion. In Matlab, use finincon with the objective function $f$ described below in section 5.e to determine $T_x$, $T_y$, $T_z$, $\theta_x$, $\theta_y$, and $\theta_z$.

Optimization Loop:

5a. Transform Surface$_1$ to Surface$_2$ using the inverse of the alignment transformation matrix (either the initial guess or that resulting from the prior iteration)

$$d_2^A = d_1^A M_{1to2} \quad (17)$$

$$n_2^A = n_1^A N_{1to2} \quad (18)$$

5b. Sample Surface$_2$ at the same [θ,z] locations as the transformed data from Surface$_1$. The set of points is $d_2^B$. The z values are the z values of $d_2^A$. The θ values are the arctangents values (a tan(y/x)) of $d_2^A$. Also calculate the normals at each point. This set of normals is $n_2^B$. If there are no corresponding points on the two surfaces because one surface extends more proximally or distally than the other, then those points may be dropped from the analysis for the iteration.

5c. Calculate the mean radial error:

$$r_2^A = \sqrt{d_2^A x^2 + d_2^A y^2 + d_2^A z^2} \quad (19)$$

$$r_2^B = \sqrt{d_2^B x^2 + d_2^B y^2 + d_2^B z^2} \quad (20)$$

$$\text{MnRadialError} = \text{mean}(r_2^B - r_2^A) \quad (21)$$

5d. Calculate the mean hyperbolic arctangent of the dot product of the normals, which is the Normal Similarity term used in the objective function:

$$\text{NormalSimilarity} = \text{mean}(\tan h^{-1}(n_2^A \cdot n_2^B - 10^{-7})) \quad (22)$$

The dot product of two parallel unit vectors is equal to 1. $10^{-7}$ is subtracted from the dot product of the normals because when the normals are parallel to each other the dot product is 1. The hyperbolic arc tangent of 1 is infinity which may distort the analysis and is thus preferably avoided.

5e. Calculate the value of the objective function:

$$f = \text{RadialWeight} \times \text{MnRadialError} - \text{NormalWeight} \times \text{NormalSimilarity} \quad (23)$$

Because the objective function is minimized within the optimization routine, the second term which maximizes shape similarity is subtracted from the first. In this optimization routine, a RadialWeight of 1.0 and a NormalWeight of 0.0 were used (as indicated above), and the translational and rotational transformation matrices calculated. They may then be used as an initial guess in the second optimization routine, step 6.

6. Run second optimization routine to completion

Repeat the optimization using the initial guess from step 5 and a RadialWeight of 0.8 and NormalWeight of 0.2. The $T_x$, $T_y$, $T_z$, $\theta_x$, $\theta_y$, and $\theta_z$ values calculated from this optimization may be the settings used in the transformation matrices to align Surface$_1$ and Surface$_2$. When a collection of surfaces are compared to a reference surface (e.g., the three test sockets to the original socket in the present study), the bounds of z that include all surfaces are determined, and data within those bounds used in analysis.

For the research study, all socket shapes for a subject were aligned within the same optimization procedure to ensure they were of the same length. To assess sensitivity to weighting of the optimization criteria in the algorithm, mean radial error results using a 0.8:0.2 ratio of minimizing volume difference to maximizing shape similarity may be compared to results using a 1.0:0.0 ratio.

Once the test socket shapes were aligned 14 to the desired socket shapes and the shapes trimmed at the brim, computational analyses may be carried out (e.g., steps 16-34). The analyses may characterize the size and shape quality of the test sockets compared with the desired sockets. The analysis may proceed in series in a manner similar to the clinical static fitting procedure described above, e.g., assessment of: (1) overall socket volume error; (2) regional socket volume error; and (3) local socket shape error. The metrics developed for each are described below.

Overall socket volume error—the global volume error for each test socket may be determined by calculating the radial error between the points on a test socket shape and the corresponding points on the desired socket shape 16. The mean radial error may then be calculated 20 as the average radial difference between each point on the test socket compared with its corresponding point (on the same radial vector) on the desired socket. Optionally, the calculated radial error may be plotted to a surface model 18 and displayed to a practitioner to facilitate socket assessment, see FIG. 6A-6C, discussed further below.

Regional socket volume error—the regional volume error may be determined by calculating the inter-quartile range (IQR) of radial error 26. IQR is the range of radial error about the MRE between the test socket shape and the desired socket shape for the 50% of the points on the surface that are closest to the mean radial error. Thus a test socket with a large IQR may have some regions on the socket that are grossly undersized and other regions that are grossly oversized, while a test socket with a small IQR may have a small and relatively uniform error over the surface.

Local socket shape error—local socket shape error may be determined by calculating the surface normal angle errors (SNAE) between the test socket shape and the desired socket shape 30. Surface normal angle error is the angle difference between a line projecting outward normal from the test socket surface and a line projecting outward normal from the desired socket surface, assuming the points are along the same radial vector directed outward perpendicular to the socket longitudinal axis (the longitudinal axis is the same for both sockets after executing the alignment algorithm described above). Thus the surface normal angle error may be a measure of local shape difference. The mean SNAE is the average surface normal angle error of all points on the surface with all points equally weighted in the calculation.

After calculating the MRE 20, the calculated MRE may be compared with a threshold MRE value 22. The threshold MRE value may be a value greater than 0.18 mm or may be, for example, in the range 0.24 mm-0.29 mm. In some embodiments, the threshold MRE is 0.25 mm. When a threshold MRE is exceeded by the calculated MRE for a fabricated socket, a practitioner may reshape or resize the prosthetic socket 24 before assessing socket fit to the patient 36. When the calculated MRE falls below the set threshold, further computational analyses may be carried out (e.g., steps 26-34). To arrive at the disclosed MRE threshold, clinical assessments of socket fit by an experienced practitioner were compared to computer-socket manufacturing errors measured with a shape-sensing instrument.

A total of eleven subjects with unilateral trans-tibial amputation participated in the study. One subject's socket was modified between the time the socket shape was digitized and the time test socket fitting was conducted. His data were excluded from the analysis described below. Of the remaining ten subjects, nine had their limb amputation as a result of traumatic injury, and one from Spina Bifida. Residual limb length from the mid-patellar tendon to the distal end of the tibia averaged 15.7 (s.d.=3.5) cm. Time since amputation ranged from 1.3 to 68.5 yr with a mean of 18.1 (s.d.=20.4) yr. Seven subjects were male, and three were female. Six were K3 level ambulators, and four were K4 level ambulators, as defined by MFCL criteria. Subject mass averaged 80.3 (s.d.=16.2) kg, and BMI (subject wearing prosthesis) averaged 25.5 (s.d.=4.7). Seven subjects used an elastomeric liner with locking pin, one an elastomeric liner with a suction socket (no pin), one a Pelite liner with sleeve suspension, and one a gel-impregnated sock with sleeve suspension. Subject reported sock ply use ranged from 0 to 6 ply, and averaged 3.7 (s.d.=2.2) ply. Time since the regular prosthetic socket was made averaged 2.0 (s.d.=1.6) yr. All subjects used a dynamic response prosthetic foot.

For nine of the ten subjects (all except subject #8), the time between when digitization of the subject's regular prosthetic socket and conducted clinical evaluations of the test socket fits averaged 66 d (s.d.=28 d) and ranged from 17 d to 98 d. Subject #8 was assessed 259 d after the socket shape was digitized. Subject #8 was tested later than other subjects because of scheduling issues and health problems. Despite the long time interval, subject #8's normally-used socket fit, like that of the other nine subjects, was deemed acceptable at the time of clinical test socket fitting.

Figure 3:
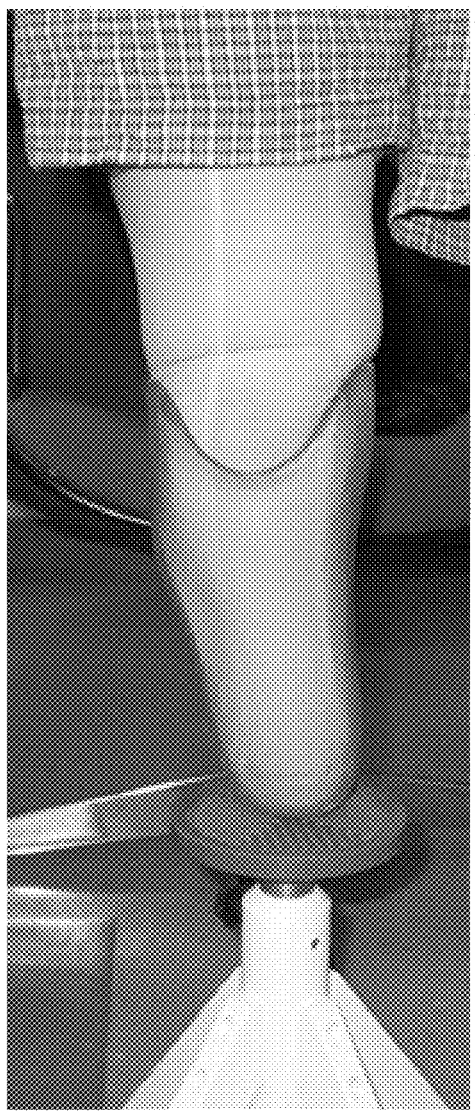
FIG. 3 shows a subject standing while bearing weight on a fitting stool during clinical assessment of the test sockets.

As discussed above, a total of 33 sockets were tested, three by each subject except subject #7 who tested six sockets (one from each central fabrication facility). For clinical assessment, the subject upon arriving at the research laboratory sat still for 10 minutes in a stable chair with the prosthesis on and the prosthetic foot supported by the floor. This procedure was performed to achieve a homeostatic condition before test fitting. The research practitioner, who had over eight years of clinical experience as a certified prosthetist and over eleven years of research experience in prosthetics, queried the subject about medical history and prosthesis history, and determined if changes had been made to the prosthesis since the socket shape was digitized. If changes had been made then they were recorded. The subject then removed the prosthesis, and the research practitioner inspected the residual limb for signs of breakdown or injury. If breakdown or injury were apparent then the subject was released from the study and encouraged to visit his or her regular prosthetist for socket modification. If no breakdown or injury were noted then the session continued and the subject, wearing the same liner and sock ply used wearing the regular prosthesis, donned the first test socket. Both the subject and the practitioner were blinded as to the facility that manufactured each test socket, and there were no distinguishing features that identified any socket's manufacturer. In each testing session, the order in which the sockets were tested was randomized. Test fitting of each socket proceeded in a manner similar to clinical static fitting. The subject was instructed to bear weight on the socket while supported on a fitting stool, as depicted in FIG. 3. The practitioner used putty balls inside the bottom of the socket to assess distal end bearing, a probe (corset stay) to identify pressure points between the residual limb and socket, verbal feedback from the subject to assess comfort and to identify problem areas, and visual inspection of skin color after doffing to assess tissue response. The practitioner documented if there was a global sizing problem (i.e., socket too large or too small). If sock addition was deemed necessary then socks were added one at a time (1-ply Soft Sock, Knit-Rite). According to manufacturer documentation, the Soft Sock was 90.6% polyester, 5% X-STATIC, and 4.4% Lycra Spandex (Invista). X-STATIC is a proprietary silver-based antimicrobial material (Noble Fiber Technologies, Inc.). Lycra Spandex is a synthetic fiber with high elasticity. The socks were new, and were not worn at any time other than during the present study. In a separate investigation we determined that this sock model had a thickness of 0.45 mm (s.d.=0.03 mm) under loading conditions representative of standing with equal weight-bearing. If two or more 1-ply socks were added or if more than two 1-ply sock thickness was deemed necessary for just the proximal region or just the distal region, in other words there was a regional socket volume problem, then the socket was considered oversized and was documented as having a "sizing and possibly shaping" problem. No further evaluation was conducted on the socket. The basis for this methodology was that in clinical practice oversizing of a new socket by two 1-ply socks would be, for a patient who does not undergo clinically-significant diurnal volume change, clinically unacceptable and require socket reduction before further test fitting. For sockets with 1-ply or no ply added, socket shape was carefully assessed, and the practitioner marked regions deemed too large or too small, if they existed, with blue (too large) and red (too small) marker on the external socket surface. The sockets were later photographed to document regions in need of shape modification. It took less than 5 minutes to assess each test socket fit. After evaluation of socket fit was completed, the subject doffed the test socket, donned his or her regular prosthesis, and stood for 2 minutes. The subject then sat down, doffed the regular prosthesis, and donned the second test socket. Fit was evaluated using the same test procedure as described above. This test was followed by a 2 minutes stand wearing the regular prosthesis. The third test socket was then evaluated in a similar manner, followed by a 2 minutes stand wearing the regular prosthesis. All three sockets were then tested again using the same procedure and in the same order. Careful records were kept of the practitioner's assessment and feedback from the subject.

Of the 33 sockets, sixteen were deemed to need sizing and possibly shaping changes; seven only shaping changes; and ten no changes. The need for change and the nature (sizing, shaping) were distributed among the subjects and central fabrication facilities as shown in FIG. 4A. Only one subject, Subject #8, needed the same type of modification (shape only) to all three sockets. Fabrication facilities c and f had fewer sockets deemed clinically to require sizing or shaping changes than the other central fabrication facilities (FIG. 4B). Facilities c and f demonstrated socket shapes strongly matched to electronic file shapes in a previous investigation.

Figure 5:
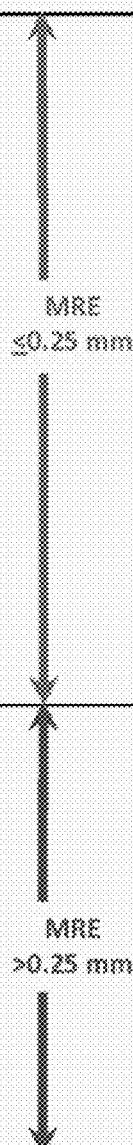
FIG. 5 shows the mean radial error and percentage volume error results for all 33 sockets ranked in order of lowest to highest mean radial error (MRE). Socket volume errors (Vol E) are expressed in percentage volume of the subject's normally-used socket with the brim trimmed.

Computed shape evaluation results (MRE, percent volume error) were integrated into a table with the clinical evaluations, as depicted in FIG. 5, and ordered the sockets from smallest to largest mean radial error (MRE). Sockets in need of sizing and possibly shaping change tended to group towards the bottom of the table. Twelve of the thirteen sockets with MRE over 0.24 mm-0.28 mm needed sizing and possibly shaping change, and one needed just shaping change. There were no sockets with an MRE greater than 0.28 mm that did not need modification. Based on the strong match between the MRE computations and clinical fitting (lower part of FIG. 5), an MRE value of 0.25 mm was selected as a possible delineator of oversized from not oversized sockets. An MRE of 0.25 mm may correspond to a socket volume error of approximately 1.0%. Eleven of the twelve sockets that needed sizing and possibly shaping change required reduction, consistent with their positive MRE value (indicating oversizing), while one required enlargement, inconsistent with its positive MRE value. FIGS. 6A-6C depict exemplary radial error plots with the x- and y-axes indicating radial and vertical distances, respectively in mm and with a scale range from −0.1 mm to +0.1 mm. FIG. 6A depicts an exemplary socket (socket 2/e) with MRE>0.25 mm clinically deemed in need of reduction and possibly shaping change. As can be seen, the socket 2/e is generally oversized. As depicted in FIG. 6B, the socket with MRE>0.25 requiring enlargement (socket 7/a) was oversized over most of its surface, except for a 15 mm diameter region over the anterior distal tibia that was undersized by approximately 0.7 mm. FIG. 6C depicts a socket (socket 10/b) with an MRE≤0.25 mm but deemed clinically in need of sizing and possibly shaping change. These sockets tended to be grossly oversized in some areas but grossly undersized in others, as shown in the example in FIG. 6C.

When a different algorithm was used to align socket shapes 14 that minimized only radial error (weighting ratio 1.0:0.0) and not both radial error and surface normal angle error (weighting ratio 0.8:0.2), the calculated MREs 20 were reduced, but not in equal proportion for all sockets, as shown by FIG. 7. The ordering of sockets from lowest to highest MRE changed for eight of the sockets, and one socket shifted from the unacceptable to acceptable category. The weighting ratio used to generate the results presented in FIGS. 4A-B, 5 and 6A-C (0.8:0.2) was used in all subsequent analysis.

A weighting ratio of 0.8:0.2 between radial weighting (Radial Weight) and normal weighting (NormalWeight) was preferred within the optimization routine by trying different ratios and assessing match with clinical assessment, both in pilot investigations of the present study and in prior investigations. The finding that results in the present study changed when exclusively minimization of radial difference was used in the alignment optimization routine (weighting ratio 1.0:0.0) indicates that introduction of minimization of surface normal angle difference, which reflected shape similarity, affected how the sockets aligned. Shapes without distinct and sharp contour changes may need the shape similarity criteria (surface normal angle) within the alignment algorithm for them to align properly. Including surface normal angle improved delineation of the type of socket fabrication problem (sizing, shaping). In general, including surface normal angle optimization in the algorithm increased differences in MRE between the sockets tested as shown in FIG. 7.

Using a selected delineation of a threshold MRE of 0.25 mm, the thirteen sockets with an MRE greater than 0.25 mm were considered well-characterized (all were deemed in need of sizing or shaping change), and were not considered in further analysis. In clinical practice, a test socket deemed too large (>two 1-ply sock additions) would typically not be further inspected but instead would be reduced 24.

The result that sockets with large MRE were deemed clinically too large indicates that MRE was a good quantitative measure of volume error, serving well to identify what the practitioner detected clinically as an improperly sized socket. For the sockets tested in the present study, an MRE of 0.25 mm reflected approximately a 1.0% volume error. Putting this volume in perspective, 0.25 mm is approximately half the thickness of a new 3-ply Soft Sock (Knit-Rite) while worn on a residual limb during walking. While it is recognized that half of a 3-ply sock may or may not affect socket comfort, this amount of oversizing at the time of new socket fitting is problematic. Clinical experience is that oversized sockets induce a greater diurnal limb volume change than properly sized sockets, and thus necessitate more patient sock changes over the day. Thus manufacturing errors that result in oversizing may inconvenience the patient. They may also influence socket longevity. Typically a patient's residual limb will decrease in volume over time, and the patient will add more socks to compensate. Once sock ply is excessive (e.g., more than approximately 10 ply), a new socket needs to be made. By being oversized at the outset when the socket is manufactured, socket longevity may be reduced.

If a calculated MRE does not exceed a set MRE threshold 22, an interquartile range of radial error (IQR) may be calculated 26. As set forth above, IQR is the range of radial error about the MRE between the test socket shape and the desired socket shape for the 50% of the points on the surface that are closest to the mean radial error. After calculating the IQR 26, the calculated IQR may be compared with a threshold IQR value 28. The threshold IQR value may be a value greater than 0.3 mm or may be, for example, in the range 0.34 mm-0.42 mm. In some embodiments, the threshold IQR may be 0.40 mm. When a threshold IQR is exceeded by the calculated IQR for a fabricated socket, a practitioner may reshape or resize the prosthetic socket 24 before assessing socket fit to the patient 36. When the calculated IRQ falls below the set threshold, further computational analyses may be carried out (e.g., steps 30-34). To arrive at the disclosed IQR threshold, clinical assessments of socket fit by an experienced practitioner were compared to computer-socket manufacturing errors measured with a shape-sensing instrument.

Figure 8:
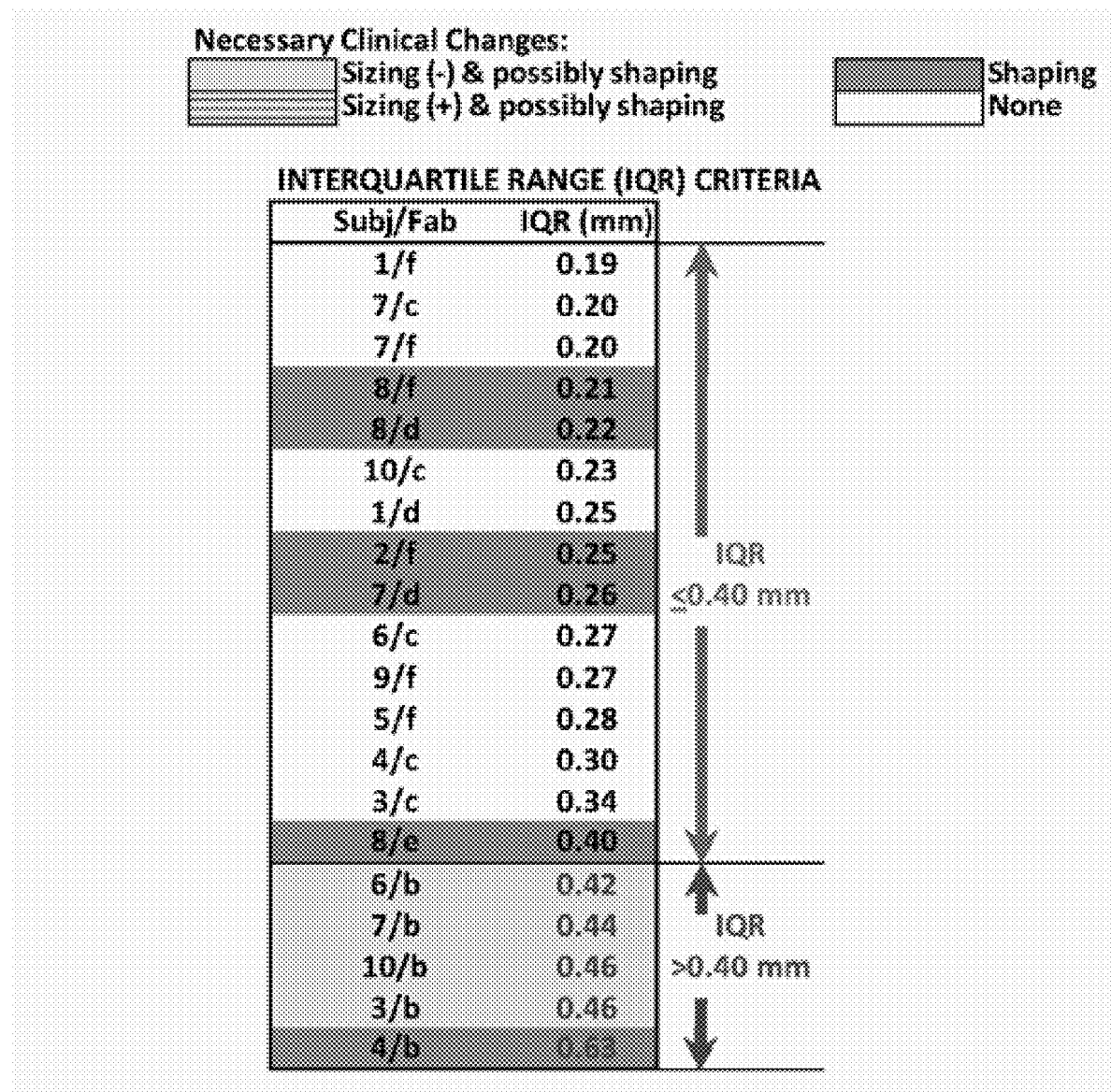
FIG. 8 shows the interquartile range results for all twenty test sockets with MRE≤0.25 mm ranked in order of lowest to highest interquartile range (IQR)
Figure 9A:
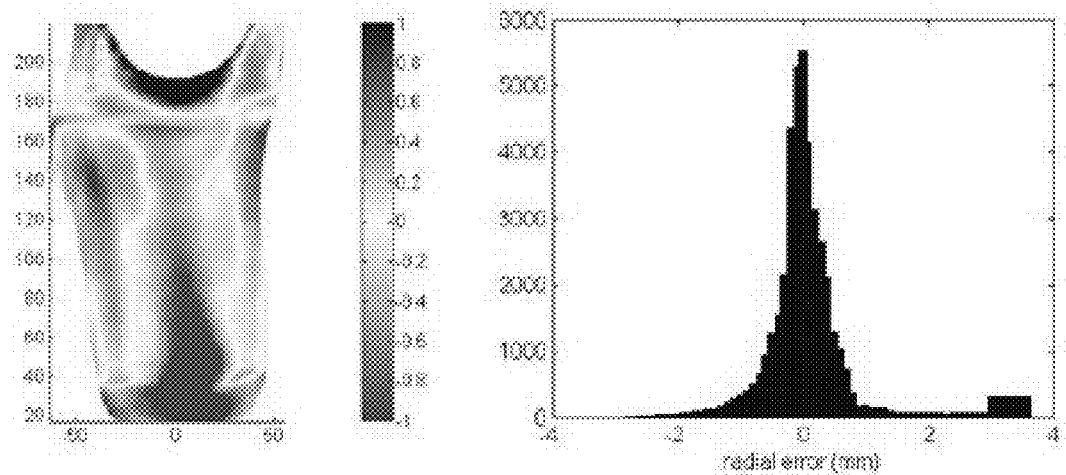
FIGS. 9A-9B show exemplary radial error and interquartile range results.
Figure 9B:
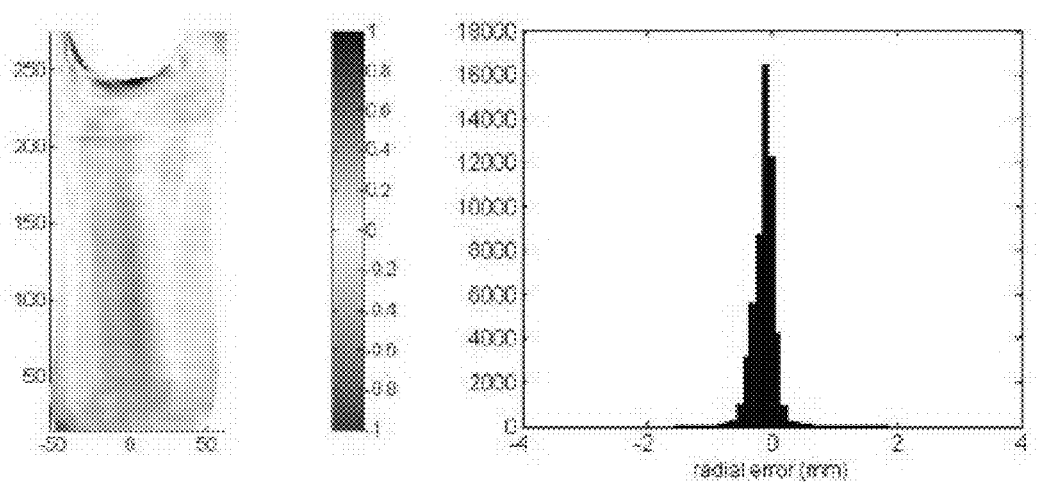

Analysis of the twenty sockets with MRE less than or equal to 0.25 mm continued. These sockets were ordered from smallest to largest inter-quartile range (IQR) as shown in FIG. 8. Sockets in need of sizing and possibly shaping change 24 tended to group towards the bottom of the table. FIG. 9A-9B compare a socket (socket 3/b) with MRE≤0.25 mm and IQR>0.40 mm with a socket (socket 1/f) which has MRE≤0.25 mm and IQR<0.40 mm. Four of the five sockets with IQR greater than 0.40 mm needed sizing and possibly shaping change, while one needed exclusively shaping change. It is noted that all five sockets with IQR>0.40 mm were fabricated by the same facility (b). All of these sockets suffered from regional volume distortions in load bearing regions, as shown in FIGS. 6C and 9A, unlike sockets with IQR≤0.40 mm which did not display this feature (FIG. 9B). The single socket deemed in need of only shaping change (6/a) in the lower part of FIG. 5 had an IQR of 0.51 mm. Thus it would have been classified in the lower group within FIG. 8 if it had not been eliminated earlier because its MRE was greater than 0.25 mm.

MRE alone did not identify all sockets with problematic fit. Additional computed metrics were needed. This result points to the complexity of prosthetic fitting. This result might be relevant to modeling efforts to predict tissue response to changes in socket design. Based on the match between the IQR computations and the clinical findings, an IQR value of 0.40 mm was selected as a preferable computed delineator of acceptable regionally-sized sockets from unacceptable regionally-sized sockets. The five sockets with IQR greater than 0.40 mm were considered well-characterized and not considered in further analysis. The result that the IQR metric picked up most of the sockets with sizing error that were not identified by the MRE criterion is consistent with the interpretation that IQR reflected a combination of sizing and shaping problems, which are termed herein as "regional volume error." A low MRE combined with a large IQR may mean that though the overall volume of the socket was good, the spread in radial error was high. In other words at least one area of the socket may be undersized and at least one area may be oversized. Thus the socket shape may be distorted. It is suspected that the practitioner identified these sockets as too big because of the location of the oversizing. All four sockets with MRE≤0.25 mm and IQR>0.40 mm that were deemed in need or sizing or shaping change were oversized on the anterior tibial flares and the posterior proximal region. Oversizing at these locations may have caused the subject's residual limb to sink deep into the socket, giving the appearance of socket oversizing during static fit testing.

The reason one facility's sockets dominated the population of sockets with low MRE but high IQR (see bottom of FIG. 8) may have been because this facility had a consistent manufacturing problem. All of their sockets tended to be too large posterior proximally and on the anterior tibial flares, but too small anterior distally. In prior investigations, more than one facility demonstrated this kind of error.

The result that companies may or may not have specific manufacturing problems points to the variability in quality in the central fabrication industry. Not all central fabrication is performed the same. The industry will improve as a whole if companies understand their specific manufacturing limitations and address them. Manufacturers of CAD/CAM equipment can facilitate this advance by incorporating tools into their products that allow customers to conduct evaluations of their socket manufacturing quality, similar to the assessment devices described here. Emerging technology, particularly high-quality small size imaging systems that allow inside socket shape to be accurately measured, may facilitate this advance.

If a calculated IRQ does not exceed a set IRQ threshold 28, surface normal angle errors (SNAE) between the surface model and desired shape may be calculated 30. As set forth above, surface normal angle error is the angle difference between a line projecting outward normal from the test socket surface and a line projecting outward normal from the desired socket surface, assuming the points are along the same radial vector directed outward perpendicular to the socket longitudinal axis (the longitudinal axis is the same for both sockets after executing the alignment algorithm described above). Thus the surface normal angle error may be a measure of local shape difference. After calculating the SNAE 30, the calculated SNAE may be plotted to the surface model 32. The plots may be displayed to a practitioner to facilitate socket assessment. It was determined that closed contour regions in the SNAE plots indicated the need for reshaping 24. However, if no closed contour regions are found in the SNAE plot, the socket may have minimal defects and a practitioner may proceed to analyze the fit of the socket to the patient 36. To arrive at this determination, clinical assessments of socket fit by an experienced practitioner were compared to computer-socket manufacturing errors measured with the shape-sensing instrument.

Figure 10:
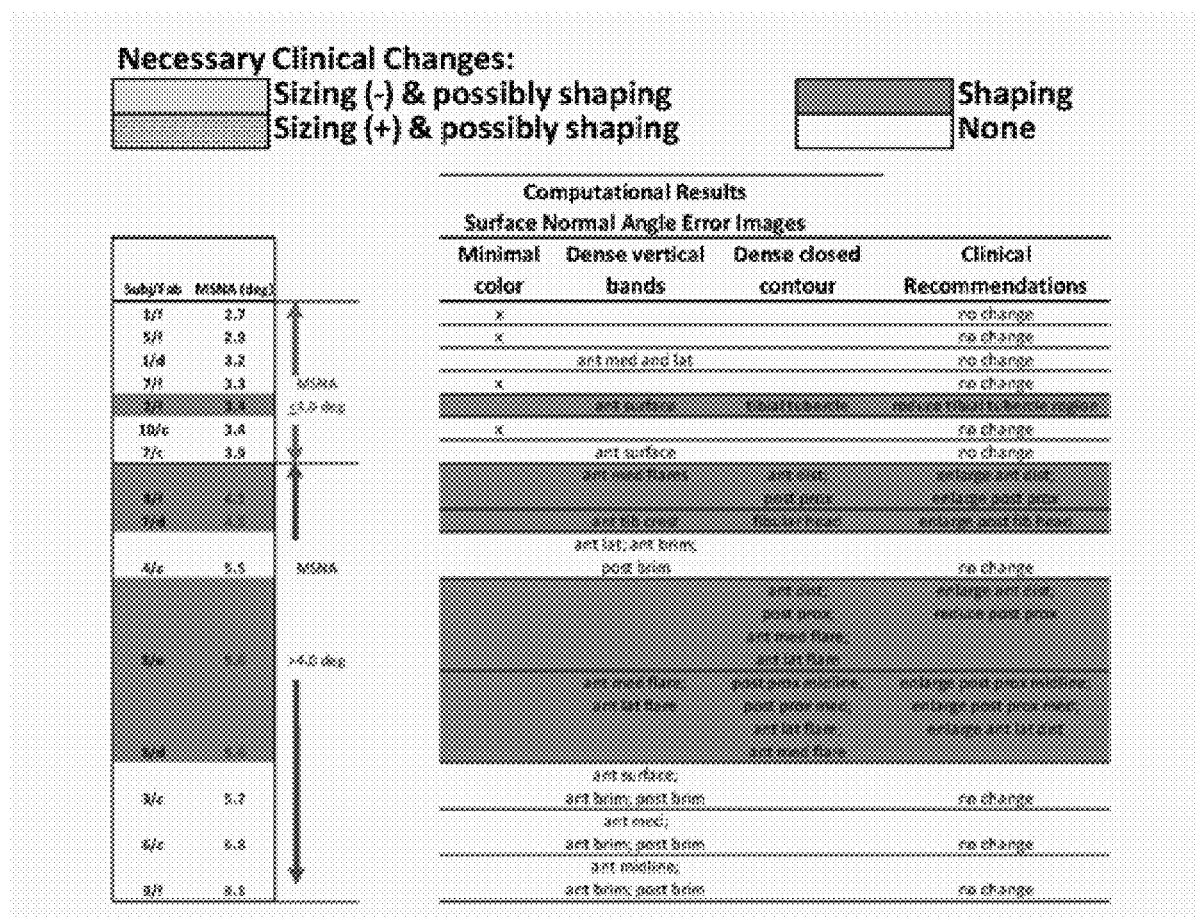
FIG. 10 shows the surface normal angle error results. The left panel shows all fifteen sockets with MRE≤0.25 mm and IQR≤0.40 mm ranked from lowest to highest mean surface normal angle error. The right panel shows the description of surface normal angle distributions and their link with clinical recommendations.

Analysis of the fifteen sockets with MREs≤0.25 mm and IQR≤0.40 mm continued. These sockets were ordered from smallest to largest mean surface normal angle error (mean SNAE) as illustrated in FIG. 10. Sockets in need of shaping modification tended to group towards the bottom of the table. Four of the eight sockets with mean SNAE greater than 4.0° needed shaping change, and four did not need change. One socket with mean SNAE less than or equal to 4.0° needed shaping change and the remaining six with mean SNAE less than or equal to 4.0° did not need any modification.

Plots of surface normal angle error distribution were inspected for the fifteen sockets to explore why some sockets deemed clinically acceptable had high mean SNAE. FIG. 11A-11C show anterior and posterior SNAE plots (left two panels) and corresponding anterior and posterior radial error plots (right two panels) for three different sockets. In the SNAE plots, the lighter regions indicate low shape differences, while the darker regions indicate greater shape differences. Each of the sockets in FIGS. 11A-11C had MREs≤0.25 mm; IQR≤0.40 mm; and mean SNAE>4.0°. The circled regions are the regions in need of shaping change. FIG. 11A shows socket (8/e) clinically deemed in need of shaping change anterior distally and posterior proximally. FIG. 11B shows socket (7/d) which is deemed in need of shaping change at the posterior aspect of the fibular head. FIG. 11C shows a socket (3/c) clinically deemed not in need of modification.

FIGS. 12A-12B show anterior and posterior SNAE plots (left two panels) and corresponding anterior and posterior radial error plots (right two panels) for two different sockets. Each of the sockets in FIGS. 12A-12B had MREs≤0.25 mm; IQR≤0.40 mm; and mean SNAE≤4.0°. FIG. 12A shows socket (5/f) which is clinically deemed not in need of change and FIG. 12B shows socket (2/f) which is clinically deemed in need of shaping change at the tibial tubercle.

Sockets with mean SNAE greater than 4.0° in need of modification (sockets highlighted in the lower part of FIG. 10) tended to show dense closed contours in regions the than 4.0° in need of modification, the closed contour regions well matched locations the practitioner deemed problematic, and the direction of radial error, visually apparent in plots of MRE (right panels in FIGS. 11A-11C and 12A-12B), was consistent with clinical assessment (FIG. 10). In other words, socket locations the practitioner identified as in need of reduction were oversized (blue) in MRE plots. Socket locations the practitioner identified as in need of relief were undersized (red) in MRE plots. However, for sockets 8/d and 8/e, there were closed contours on the flares that were not identified problematic by the research practitioner, FIG. 10. Sockets with mean SNAE greater than 4.0° not in need of modification (sockets in the lower part of FIG. 10 and not highlighted) tended to have much error at the brim and linear bands of high surface normal angle error elsewhere. They did not show closed contour regions as shown in FIG. 11C. Sockets with mean SNAE less than or equal to 4.0° not in need of modification (sockets in the upper part of FIG. 10 and not highlighted) showed low color densities as shown in FIG. 12A. The single socket with a mean SNAE less than 4.0° but in need of clinical modification (sockets highlighted in the upper part of FIG. 10) showed a dense closed contour at the tibial tubercle, the site deemed clinically to need modification as shown in FIG. 12B. Thus regions with dense closed contours were clinically problematic while a socket with no closed contours was acceptable fit.

A comparison of plots of surface normal angle error distribution (FIGS. 11A-11B left panels) with plots of radial error distribution (FIGS. 11A-11B, right panels) showed that high surface normal angle errors tended to concentrate at locations of high change (gradient) in radial error. Surface normal angle error reflected the curvature mismatch at the boundary of the more oversized to less oversized region, or more undersized to less undersized region.

The mean SNAE metric, unlike the MRE and IQR metrics described above, mischaracterized some of the socket clinical fits as shown in FIG. 10. These mischaracterizations may have reflected measurement error in the proximal region of the socket where a different measurement instrument was used. An additional issue was the need to assemble data from two instruments (Provel digitizer; our custom digitizer) within this region. All four of the sockets with mean SNAE greater than 4.0 degrees but deemed clinically acceptable (lower part of FIG. 10) had high surface normal angle errors at the brim. It is noteworthy that brim errors were not sufficient to distort MRE or IQR calculations and interpretations, but they did affect mean SNAE. This happened because surface normal angle was a more sensitive measure to slight mismatches in shape than were MRE and IQR. Thus while surface normal angle error was a very sensitive measure and served well to identify local shape errors, it was detrimentally affected by digitization error at the brim.

Closed contours of high surface normal angle error matched regions identified clinically in need of shape modification. A more accurate representation of the surface may be achieved and presence of vertical lines in SNAE plots reduced if corrections were made in three dimensions.

The finding that clinically detected local socket shape problems matched well with dense closed contours of surface normal angle error, as shown by FIGS. 10, 11A-11C, and 12A-12B, provides insight into the nature of clinically relevant shaping problems. A closed contour of high surface normal error is a regional distortion, i.e. a pushed-in or pulled-out contour on the socket surface as illustrated by FIG. 13A-13B. This distortion is different from that of a line of high surface normal angle error, which would be a ridge rather than a closed contour. Interface stresses will focus within the contour for the pushed-in case (FIG. 13A), and at the perimeter for the pulled-out case (FIG. 13B). Because stresses for the pulled-out case are likely higher at the edge of the contour than within it, the pulled-out case may generate a sensation of excessive pressure to the patient at the perimeter of the region. Subject #8's socket e, for example, demonstrated this result. This interpretation may help explain why designing an acceptable socket shape is so difficult, and how quantitative assessments as described here may facilitate understanding of the clinical manifestations of shape error. While one's initial inclination for a patient voicing localized pain might be to relieve the affected area of the socket, if a pulled-out error resulting from poor manufacturing is the source, then relieving the area may worsen fit rather than improve fit. The pulled-out region should be pushed in so that stress is tolerated within the region rather than just at its perimeter. In a computational sense this interpretation points to the importance of identifying high gradients of MRE rather than just identifying high MRE or high SNAE point locations. Locations of clinically-deemed poor fit for sockets listed in FIG. 10 were not necessarily at locations of high MRE or high SNAE but instead at regions where high SNAEs formed a closed contour. It may be possible to correct these regions using heat forming modification and then see if the clinical fit evaluation improves.

While the study excluded subjects with dysvascular cause of amputation and subjects who commonly experienced substantial diurnal volume change, some methods of the present invention may still be applicable to such subjects. These subjects may be less tolerant to sizing and/or shaping error and thus may require different computational acceptability criteria, however aspects of the present invention, such as SNAE plots to the surface model, may facilitate objective assessment of manufactured prosthetic sockets. Further, the methods and systems disclosed herein may be useful in assessing the fit of sockets produced for both legs and arms, for orthoses (i.e., devices that support rather replacing body parts, such as spine orthoses, limb, and foot orthoses, and shoe inserts), and for other related tasks.

Because companies in the study who demonstrated the greatest percentage of acceptably fit sockets were the same facilities that demonstrated socket shapes well-matched to electronic file shapes in prior investigations, there may not be inconsistency in quality in the entire CAD/CAM industry. Instead, some facilities may consistently practice the art of socket fabrication better than others. This is important because it suggests that the nature of the error by a specific company in fabricating a properly fitting socket might be used to determine how to correct such errors in the fabrication process by modifying the electronic data shape file before it is used in the fabrication process so that the resulting socket has minimal error and closely matches the desired design socket shape.

Figure 14:
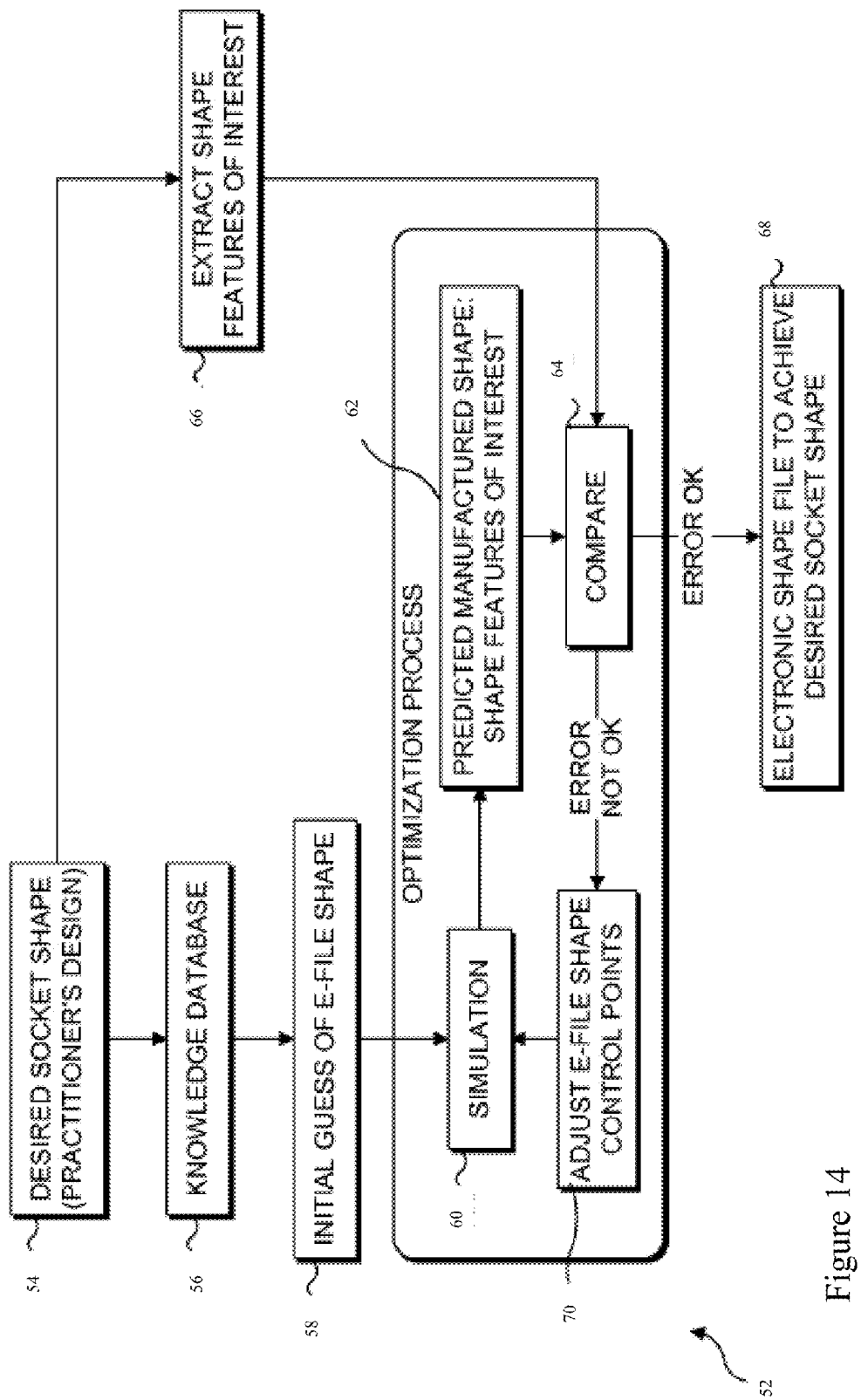
FIG. 14 illustrates an exemplary method of adjusting socket design based on simulated socket manufacture.

By measuring errors in the fit of a characteristic sampling of the sockets produced by a specific fabricating company, it may be possible to determine corrections that can be applied to the desired design electronic data file before a socket is fabricated by the company so as to ensure that the resulting socket actually closely matches the desired design shape for the socket. FIG. 14 illustrates a flowchart 52 that illustrates exemplary steps which may employ the present novel approach to achieve a solution to the "inverse" problem, i.e., it shows the steps used to determine corrections that can be applied before a socket is fabricated so that the socket that is actually produced and provided for fitting to a patient achieves an acceptable match with the desired socket shape that was originally designed. The procedure begins with a step 54, in which a desired socket shape is created that represents the practitioner's design for a specific patient residual limb. This desired socket shape is defined in an electronic data file format and can be efficiently created using a CAD program, as noted above. A step 56 provides for input of the desired socket shape to a knowledge database, which is a collection of electronic-shape-file/actual-socket-shape pairs that were established based on experimental measurements and evaluation of a plurality of sockets produced by a specific socket manufacturing system or source (i.e., a carver and forming method) that is being used to produce the current prosthetic socket. The desired socket shape is compared with the actual socket shapes within this database to select a best match. This may be done using the alignment algorithm described above. It may be necessary to linearly scale the actual socket shapes in this comparison so that both volume and shape match well with the desired socket shape. Once the best match actual socket shape is identified, its corresponding paired electronic shape data file is used in a step 58, as an initial guess of the appropriate electronic data file to be input to the optimization process.

In a step 138, the fabrication process may be simulated. A simulation engine used in this step may implement a transfer function that characterizes the changes in key features of the input electronic file shape when it goes through the manufacturing process at the specific fabricator facility. Certain anatomical regions of a socket shape may be chosen which that may be weighted to closely match the same regions in the desired socket shape. The simulation engine is a general algorithm, although it is expected that the constants used for the actual manufacturing suite being used will be tuned to achieve better results, as experience dictates. Tuning may be done using the same data used to develop the knowledge database described above in step 56, although once tuned for a particular product, the tuning should not need to be changed unless that system is modified. It is contemplated that initially, approximately five measured socket shapes/ electronic file shape pairs may be necessary to conduct this tuning.

The simulation may be developed using one of the following modeling approaches: parametric analysis; finite element analysis; fuzzy logic; neural networks; or some other artificial intelligence approach. The results of the simulation provide the predicted manufactured shape in a step 56, defined in terms of the shape features of interest related to the anatomical regions. The features assessed in this simulation are those clinically relevant to establishing a correct socket shape; weighting can be applied to various features based upon their relative importance in achieving a good fit for a socket. For example, the shape features of interest may include:

1. Distances Between Landmark Points: The landmark points may include the midpoint of the patellar tendon bar; apex of the fibular head; apex of the curve at the anterior distal end; and mid-point of the popliteal fossa. It should be noted that many other landmarks are often used in commercial socket design that could alternatively be used in the present approach. For example, other lower limb landmarks include: Anterior tibial crest, tibial tubercle, fibular head, distal end of fibula, popliteal fossa, medial and lateral femoral condyles, hamstring tendons, (the following are all for trans-femoral amputees) femoral end, femoral shaft, ischium, greater trochanter. Lower extremity orthotic related anatomical landmarks (in addition to the prosthetic related): medial and lateral malleolus, navicular, base of the $5^{th}$ metatarsal, $1^{st}$ metatarsal.

2. Sectional Volumes: The socket shape is segmented into parallel slices perpendicular to the socket long axis. The slice thickness might be smaller in highly sensitive regions (e.g., between the patellar tendon and tibial tubercle) compared with less sensitive regions. Approximately eight sections may be employed, as appropriate.

3. Regional Shapes: Preferably Four regions on the socket well match the designed socket shape: patellar tendon, fibular head, anterior distal end, and popliteal fossa. Each region is characterized by a surface area, maximum radius, and volume. Other possible regions include: tibial plateau, anterior tibial crest, tibial tuberosity, fibular shaft, distal end of fibula, tibial flares, popliteal area, posterior mid-limb, condyles, and brim.

A step 64 then compares the shape features of interest for the predicted manufactured shape from the simulation and the shape features of interest that were extracted in step 66, from the original desired socket shape created by the practitioner in step 54. The first goal is to characterize the error determined by this comparison. If the error is acceptable (i.e., below a threshold that was established based on clinical experience) then the process is done, and the electronic shape data file selected in step 58 can be used for actually manufacturing the socket, as indicated in a step 68. However, if the error is unacceptable (i.e., outside the threshold), the process determines the control points that need adjustment in a step 70. (The control points are the points that characterize the predicted manufactured shape; a tensor product B-spline is currently used). This step also determines the direction to move the control points so as to reduce the error. It is expected that local shape modifications (i.e., the regional shapes in the list above) will require only local modification of control point locations. Because of a B-spline property known as "local control," wherein a control point only affects the nearest four segments for a cubic B-spline, specific regions can be selected and modified to change an effect they have on the predicted socket shape, while other areas are ignored so that their shape is left unchanged. The sectional volumes will likely require modification to control points within each section. The distances between landmark points will likely require a more global resizing. A new (i.e., modified) electronic shape data file will thus be created based on these adjustments. That data file is then run through the simulation procedure in step 60, and the optimization process is repeated until the error resulting is acceptably low, leading to step 68.

The preceding procedure for determining an appropriate electronic shape data file to be used before a socket is fabricated by a specific fabricating company (so as to correct errors introduced during the fabrication process by that fabricating company) thus avoids the delay resulting from the company producing an improperly fitting socket that must be either remade or modified to properly fit a patient's residual limb (or which may require an excessive number of socks be worn to achieve a less than perfect fit for the patient).

It is contemplated that the solution to this inverse problem might be further simplified if the sockets are represented with a recently introduced method of representing surfaces called T-splines. With T-splines, it should be possible to represent surfaces as accurately as a tensor product B-spline but with about one-third the number of control points.

In creating the desired socket shape 54, it may be important to factor in the influence of prior activity towards cast shape or to control the amount of prior activity experienced by a patient prior to residual limb casting. Practitioners may consider the time of the day at which the cast of an individual is collected, as well as what the individual was doing earlier in the day before coming to the clinic for casting. These variations may strongly affect the shape outcome from casting, which will impact the fit of the prosthetic socket on the residual limb. Prior ambulation, running, or other activity may generally increase residual limb volume however the shape differences may be non-uniform over the limb surface. Accordingly, cast volume may be influenced by doffing time and prior activity. Thus it may be preferable for a practitioner to factor in doffing time and prior activity or to control doffing time and prior activity prior to residual limb casting.

Figures 15, 16:
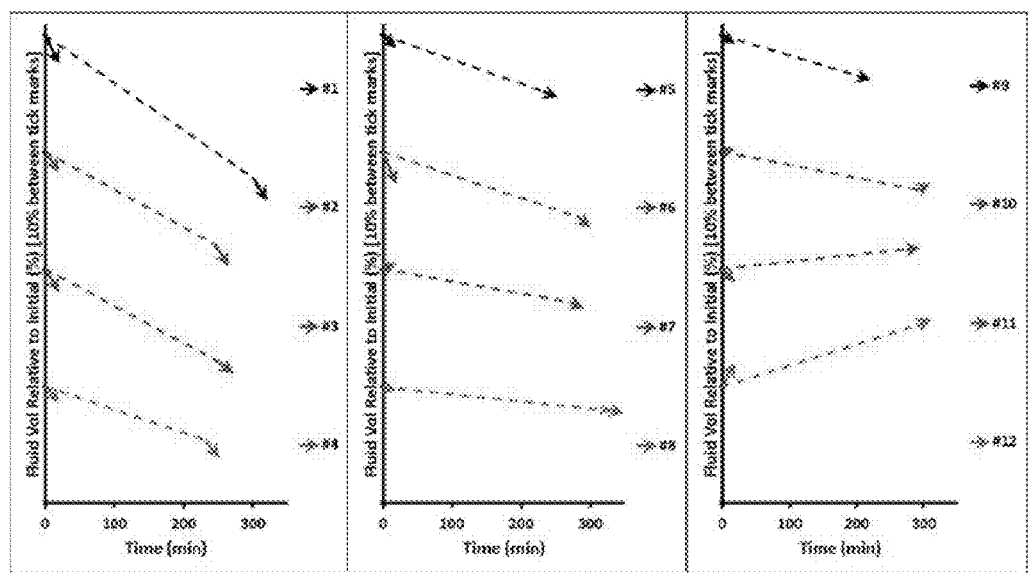
FIG. 15 shows exemplary ranges of percent volume change during morning and afternoon activity sessions and for the time period between activity sessions.
FIG. 16 shows percent volume change for individual patients during morning and afternoon activity sessions and for the time period between activity sessions.

Further, residual limb fluid volume may change during the day. FIG. 15 shows the results of a study which measured % volume change during morning activity sessions, afternoon activity sessions, and the time period between the activity sessions. As shown by the study, rate of fluid volume change during morning sessions of sitting, standing, and walking ranged from −8.5%/h to 5.9%/h (median: −2.2%/h). The rate of fluid volume change between morning and afternoon sessions of activity ranged from −2.7%/h to 0.9%/h (median −1.0%/h). The fluid volume change during afternoon sessions of sitting, standing, and walking ranged from −5.5%/h to 1.6%/h (median −1.8%/h). FIG. 16 shows the percent residual-limb fluid volume change versus time for all subjects tested. Arrowed lines illustrate within-session fluid volume changes (morning and afternoon) and dashed lines represent between-session changes. Subjects are ordered from least to greatest between-session rate of change.

Rate of fluid volume change during a day may be affected by sitting, standing, and walking activities, presence of peripheral arterial complications; being female; time since amputation; and wearing the socket without doffing for extended periods of time. Further subjects with peripheral arterial complications and female subject may have greater fluid volume loss rates throughout a day. Subjects who have had their limb amputation for greater than 5 years may also experience greater loss rates than those with amputation for less than 5 years. Food and liquid intake, and the presence and duration of periods of prosthesis doffing may also affect the rate of fluid volume change. For example, because subjects lost fluid volume between sessions when they were minimally active, the result suggests that factors other than activity induced between-session fluid volume losses. It may be that wearing the socket without doffing for extended periods contributed to the residual-limb fluid volume decrease that occurred between sessions. With the socket donned, interstitial pressures may be elevated, reducing arterial to interstitial fluid transport and increasing interstitial to venous fluid transport. The net result is a fluid volume loss. A subject's posture while sitting might also reduce residual-limb fluid volume if major vessel was restricted for a prolonged interval.

In the study, the absolute rate of residual limb fluid volume change tended to be larger in the AM than in the PM, though this pattern did not occur in all subjects. The trend of greater rate of fluid volume loss during periods within sessions of high activity than between sessions with presence of peripheral arterial complications is consistent with physiological changes induced by arterial difficulties. Arterial complications may restrict fluid transport from the arterial vasculature into the interstitial space during activity, thus off-balancing it with fluid transport from the interstitial space into the venous system. More fluid may leave than enter the interstitial space because of insufficient arterial drive, unlike unaffected individuals who increase arterial drive during activity. These changes in residual limb volume throughout a day may detrimentally affect the quality of prosthesis fit and the prosthesis user's skin health. Patients may be required to add socks when the prosthesis feels loose. Accordingly, socket creation and design may factor in the effects of residual-limb volume fluctuation. Thus in some instances, the time of day for casting a patient's residual limb may be accounted for or controlled. For example, it may be better to avoid casting during the morning. Further, for subjects who show factors of greater rates of volume change, adjustments may be made to minimize the impact of volume change, for example by adjusting socket size or by adjusting the time of residual limb casting.

Figure 17:
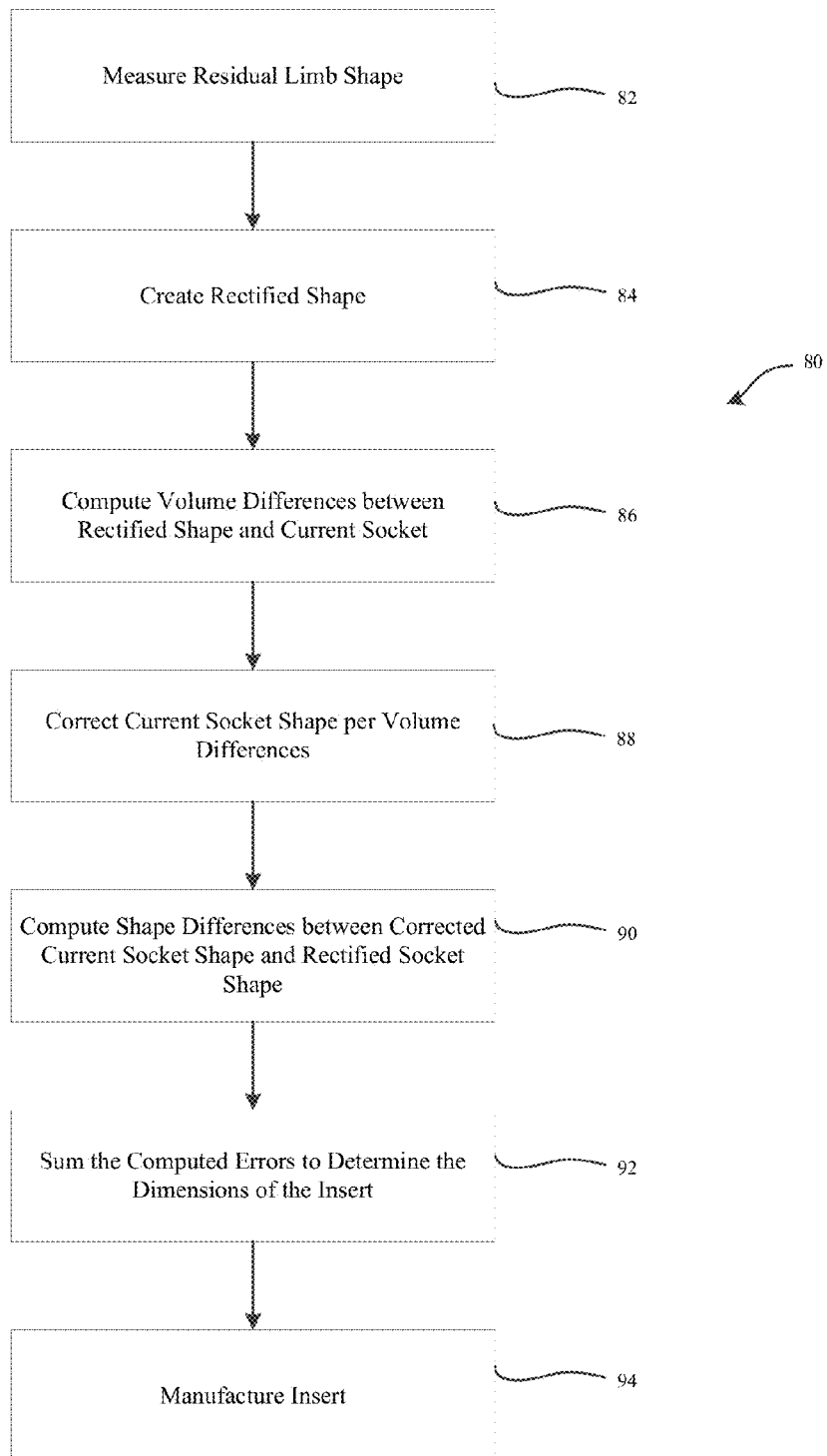
FIG. 17 illustrates an exemplary method of modifying a user's existing prosthetic socket.

In some embodiments of the invention, a method is provided for modifying the patient's existing prosthetic socket after the patient's limb has changed shape over time. This is a common and major problem with prosthetic users. FIG. 17 illustrates an exemplary method 80 for making the adjustments. At step 82, the residual limb may be measured. At step 84, a rectified shape is created from the measured shape. At step 86, a volume difference between the rectified shape and the patient's current socket shape is computed. At step 88, the current socket shape may be adjusted per the volume difference. At step 90, shape differences between the volume-corrected current socket shape and the rectified shape may be calculated. At step 92, the computed differences in shape may be summed to determine the appropriate dimensions of a socket insert or pad. At step 94, the insert or pad may be manufactured per the computations and affixed to the inside of the patient's current prosthetic socket.

By comparing the rectified shape to the current socket, a practitioner may then be able to fabricate a polymer or other flexible lightweight material insert that goes inside the current/existing socket that modifies the existing socket shape. The external shape of the insert may match the existing socket shape. The inside shape of the insert may match the new or desired socket shape established from the computational analysis. Thus the thickness of the insert shape may be controlled at different locations. Advantageously, this insert may alleviate the need for the manufacture of a new prosthetic. Prosthetic limb users may save a lot of costs by modifying existing prosthetic sockets with pads or inserts using the methods disclosed herein rather than making an entirely new socket. New sockets may cost $15,000 or more. The practitioner also saves time and costs since the practitioner may not have to make attachments, couplings for a new socket, align it, etc. If the insert adds excessive weight to the prosthesis, then the original socket shape may be modified by adding holes or removing regions, for example, so that a skeleton socket that supports the insert remains. With the use of flexible inserts, the holes may serve as a means for allowing the socket shape to be increased or decreased in volume via use of a mechanism attached to the outside of the socket that presses in or pulls out the insert. Using additive fabrication techniques, an insert may be made of different polymer material locally, according to local mechanical needs, e.g., flexibility, etc.

The residual limb shape may be measured 82 by casting or by scanning with a scanning device for example. At step 84, a rectified shape is created for comparison with the patient's current socket shape. The rectified shape may correspond to a desired socket shape and may be created in a number of ways. For example, after a prosthetist casts the patient's residual limb and while the plaster is drying, the prosthetist may push in the cast at locations intended to tolerate load, e.g., patellar tendon, tibial flares, popliteal fossa. The inside shape of the plaster cast may correspond to the rectified shape or at least a starting point for the rectified shape. The shape may be further modified based on the practitioner's experience (e.g., using a mechanical file of a positive mold or modifying the digital file on the computer) but at least it is a starting point of rectification. In another method of creating the rectified shape 84, a scan of the residual limb may be obtained 82 with a scanning device such as a laser scanner, optical scanner, or other imaging device. The scan of the residual limb may then be changed into a rectified shape. In some situations when a patient is wearing a prosthetic liner, sock or other compression type device during scanning, computer algorithms may be used to modify the scan to create the rectified shape. Several computer algorithms are known in the industry. For example, an algorithm may uniformly reduce the socket by a consistent percentage over the limb surface. Another algorithm may apply greater rectification to load tolerant areas and less to sensitive areas based either on morphometric analysis of the limb shape or based on information input by the practitioner. Additionally some software is available that may allow practitioners to create their own style libraries that learn from prior designs to impose the practitioners design styles on new cases.

The rectified shape may be compared to the current socket shape to determine whether a new socket is needed or whether the existing socket can be modified to fit the patient correctly. In situations where the existing socket can be modified, a practitioner may be able to determine what modifications are needed to the current socket by using the methods described above for determining the volume and shape differences between two shapes. For example, a practitioner may determine that over time, the person's residual limb has reduced in volume and/or they need a socket shape that is pushed in at certain locations more than others.

A two-step computational procedure may be used similar to what was described above—address (a) the volume differences first and then (b) any shape differences. The volume difference may be computed 86 between the rectified shape and the current socket shape by aligning the rectified socket shape and the current socket shape and then computing the difference between corresponding points on each shape. A volume difference may be addressed on a computer by reducing the current socket shape a uniform radial distance. Alternatively, regions of rectification, areas known in the industry to be standard locations for modification or custom regions developed by the practitioner in the computer software library, may be weighted differently. For example, rectification regions over bone may be reduced in radial dimensions less than those over soft tissues. This may be done using a computer algorithm described above. Once that is done, a computation may be run again to determine shape errors 90 between the volume-corrected current socket shape and the rectified socket shape. The regions where shape is in error may be modified according to results from the algorithm. The socket shape may be reduced in radial dimension in regions where the computational analysis identifies closed contour regions that projected outward. Conversely, the socket shape may be increased in radial dimension in regions where the computational analysis identifies closed contour regions that project inward. The amount of radial dimension change may be dictated by results from the analysis and may be scaled by a factor for different regions. Regions over bone may be weighted and thus reduced in radial dimension less than those not over bone.

Thereafter, the errors may be summed 92 to determine the dimensions of the insert over its entire surface. Then the insert may be fabricated 94 and affixed to the inside of the socket. Such inserts can be made using traditional clinical techniques or could be made using computer-aided fabrication methods, for example, additive fabrication, selective laser scintering, 3D printing, or some other procedure. Selective laser scintering is emerging in the industry. The inserts may comprise flexible thin polymer. Thus, according to some methods of the present invention, a practitioner may take advantage of the strength of additive fabrication (e.g., its accuracy) but may avoid its weakness (e.g., weak mechanical properties). Alternatively, the computed information may be used to make pads which can be affixed to the inside of the socket. The pads could be made using traditional clinical techniques, a CNC mill, additive fabrication or other manufacturing procedures.

It is also contemplated that the method for effectively designing a prosthetic socket described above may be used to accomplish an effective design without using a patient's prior socket. The limb shape may be compared to a proposed socket shape. The proposed socket shape may then be modified per the comparison. This comparison may proceed by comparing the residual limb shape with a rectified socket shape using a computer algorithm as described above. Many such algorithms are currently available in the industry. Some apply rectifications in the standard rectification locations used in the industry for manufacturing of traditional non-computer manufactured sockets. These rectification regions may be specified based on the shape of the residual limb and the locations of fiducial markers, for example at the end if the tibia, tibial tubercle, patellar tendon, and fibular head identified in the limb shape data file. Comparison between the rectified socket shape and the residual limb shape may performed and a volume difference calculated. If the volume difference is above a specified threshold value, expected to be between 0.1% and 10%, but most likely to be 3% then the proposed socket shape (the rectified shape) should be modified. The threshold volume may vary among individuals and may be dependent on what time of day and how long since doffing the prosthesis the scan was taken, and if the prosthetic liner was worn on the limb while scanning. If the prosthetic liner was on the limb while scanning then the threshold volume will be lower. The threshold volume difference may be important because a socket that is too small may reduce residual limb volume over the day, weeks, and months even when the person is not ambulating. A socket too small in volume will may cause the need for a new socket shape to be made sooner than a socket of proper volume. If the threshold volume error is exceeded then the socket shape may need to be modified to accomplish a proper volume. Data of the shape difference between the residual limb and proposed socket shape may be used to adjust the shape so that the appropriate volume difference is achieved. The closed contour regions between the shapes may be identified per the methods described above. The radial dimensions of the proposed socket shape within the contours may be adjusted to accomplish a new proposed socket shape. Each contour may be weighted. Region within some contours may be reduced in radial dimension by more than regions in other contours. The radial dimensions may be adjusted and then the comparison between the residual limb shape and the new proposed socket shape repeated. The process continues until a socket of proper volume is accomplished.

For a variable volume socket, the scanned residual limb shape volume may serve as a maximum volume for the variable volume socket. This may be the volume for conditions of rest without weight-bearing on the prosthesis. This condition allows residual limb fluid volume to be recovered or maintained compared with the reduced socket volume condition. The socket shape for the reduced socket volume conditions (necessary during weight-bearing) may be established using results from the shape comparisons described above. Area with the closed contours that identify the shape differences between the limb shape and the socket shape may be reduced in radial dimension when the person weight bears so that the variable volume socket is reduced in volume. Each contour may be weighted such that areas with higher weighting are pushed in more than areas with low weighting. Areas over bone may be weighted less than areas over soft tissue, for example. Once the person relieves weight bearing and sits down to rest the socket may be increased in volume so as to allow fluid volume recovery.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims presented will define the scope of the invention and that methods and structures within the scope of these claims and their equivalents be covered thereby.

What is claimed is:

1. A method of assessing a prosthetic socket shape for receiving a residual limb of a patient, the method comprising:
    calculating surface normal angle errors between points on a first digital model and corresponding points on a second digital model, the first digital model corresponding to the prosthetic socket shape and the second digital model corresponding to a desired shape;
    plotting the calculated surface normal angle errors to a surface model; and
    displaying the plotted surface normal angle errors to an operator;
    accepting or rejecting the prosthetic socket shape in response to the plotted surface normal angle errors;
    calculating an average radial difference between points on the first digital model and corresponding points on the second digital model and determining whether the mean radial error is above or below a set threshold;
    wherein the set threshold has a value between 0.24 mm and 0.29 mm.

2. A method of assessing a prosthetic socket shape for receiving a residual limb of a patient, the method comprising:
- calculating surface normal angle errors between points on a first digital model and corresponding points on a second digital model, the first digital model corresponding to the prosthetic socket shape and the second digital model corresponding to a desired shape;
- plotting the calculated surface normal angle errors to a surface model; and
- displaying the plotted surface normal angle errors to an operator;
- accepting or rejecting the prosthetic socket shape in response to the plotted surface normal angle errors;
- determining whether an interquartile range of radial error is above or below a second threshold.

3. The method of claim 2, wherein the second threshold value has a value between 0.34 mm and 0.42 mm.

4. The method of claim 2, further comprising the step of regionally reshaping or resizing the prosthetic socket shape when the interquartile range of radial error is above the second threshold value.

5. A method of objectively assessing a prosthetic socket shape, the method comprising:
- aligning a first digital model with a second digital model using an alignment function, the alignment function at least depending on a volume difference between the first digital model and the second digital model, the first digital model corresponding to the prosthetic socket shape and the second digital model corresponding to a desired shape;
- calculating an average radial difference between points on the first digital model and corresponding points on the second digital model; and
- determining whether the mean radial error is either above or below a first threshold, the first threshold having a value between 0.24 mm and 0.29 mm; and
- resizing or reshaping the prosthetic socket shape when the mean radial error is above the first threshold.

6. The method of claim 5, further comprising the step of scanning an interior surface of the prosthetic socket shape to create the digital model of the interior surface.

7. The method of claim 5, further comprising determining whether an inner quartile range of radial error is above a second threshold value when the mean radial error is below the first threshold value.

8. The method of claim 7, further comprising the steps of:
- resizing or reshaping the prosthetic socket shape when the interquartile range of radial error is above the second threshold;
- calculating surface normal angle errors between points on the first digital model and corresponding points on the second digital model; and
- plotting the calculated surface normal angle error to a surface model when the interquartile range of radial error is below the second threshold.

9. A method of objectively assessing a prosthetic socket shape, the method comprising:
- calculating radial differences between points on a first digital model and corresponding points on a second digital model, the first digital model corresponding to the prosthetic socket shape and the second digital model corresponding to a desired shape; and
- determining whether an interquartile range of radial error is above a threshold value, the threshold value having a value greater than 0.3 mm; and
- regionally reshaping or resizing the prosthetic socket shape when the interquartile range of radial error is above the second threshold value.

10. A method of objectively assessing a prosthetic socket shape, the method comprising:
- scanning an interior surface of a prosthetic socket shape to create a first digital model;
- calculating radial differences between points on the first digital model and corresponding points on the second digital model, the first digital model corresponding to the prosthetic socket shape and the second digital model corresponding to a desired shape; and
- determining whether an interquartile range of radial error is above a threshold value, the threshold value having a value greater than 0.3 mm.

11. The method of claim 9, wherein the threshold has a value between 0.34 mm and 0.42 mm; and
- wherein the method further comprises the step of:
- plotting surface normal angle errors between the first digital model and the second digital model to a surface model when the interquartile range is below the threshold.

12. A non-transitory computer readable media, comprising:
- an alignment module for aligning a first digital model with a second digital model based at least on a volume difference between the first digital model and the second digital model, the first digital model corresponding to the prosthetic socket shape and the second digital model corresponding to a desired shape;
- an analysis module configured to calculate surface normal angle errors between points on the first digital model and corresponding points on the second digital model and configured to plot the surface normal angle errors to a surface model;
- wherein the analysis module is further configured to calculate radial errors between points on the first digital model and corresponding points on the second digital model and to determine whether an interquartile range of radial error exceeds an interquartile range threshold.

13. A non-transitory computer readable media for assessing a prosthetic socket shape, the system comprising:
- an alignment module for aligning a first digital model with a second digital model based at least on the a volume difference between the first digital model and the second digital model, the first digital model corresponding to the prosthetic socket shape and the second digital model corresponding to a desired shape;
- an analysis module configured to calculate an average radial difference between points on the first digital model and corresponding points on the second digital model and configured to determine whether the mean radial error is either above or below a set threshold, the threshold having a value between 0.24 mm and 0.29 mm.

14. A non-transitory computer readable media for assessing a prosthetic socket shape, the system comprising:
- an alignment module for aligning a first digital model with a second digital model based at least on a volume difference between the digital model and the desired shape, the first digital model corresponding to the prosthetic socket shape and the second digital model corresponding to a desired shape;
- an analysis module configured to calculate radial differences between points on the first digital model and corresponding points on the second digital model and configured to determine whether an interquartile range of radial error is either above or below a set threshold, the threshold having a value greater than 0.3 mm.

15. The non-transitory computer readable media of claim 14, wherein the threshold has a value between 0.34 mm and 0.42 mm.

16. A non-transitory computer-readable storage medium comprising a set of computer executable instructions for facilitating clinical assessment of a prosthetic socket shape, wherein the execution of the instructions by a computer processor causes the processor to carry out the steps of:
aligning a first digital model with a second digital model using an alignment function, the alignment function at least depending on a volume difference between the first digital model and the second digital model, the first digital model corresponding to the prosthetic socket shape and the second digital model corresponding to a desired shape; and
analyzing the socket shape by performing at least one of the following:
calculating an average radial difference between points on the first digital model and corresponding points on the second digital model and providing a first signal when the mean radial error exceeds a first threshold, the first threshold having a value greater than 0.18 mm;
calculating radial differences between points on the first digital model and corresponding points on the second digital model and providing a second signal when an interquartile range of radial error is above a second threshold, the second threshold having a value greater than 0.3 mm; and
calculating surface normal angle errors between points on the first digital model and corresponding points on the second digital model and plotting the calculated surface normal angle errors to a surface model;
outputting at least one of the first signal, the second signal, and the surface model to an operator.

17. The non-transitory computer-readable storage medium of claim 16, wherein the steps further comprise receiving the first digital model from a scanning system.

18. The non-transitory computer-readable storage medium of claim 16, wherein the first threshold value is between 0.24 mm and 0.29 mm.

19. The non-transitory computer-readable storage medium of claim 18, wherein the second threshold value is between 0.34 mm and 0.42 mm.

* * * * *